(12) United States Patent
Stamler et al.

(10) Patent No.: US 7,112,563 B2
(45) Date of Patent: Sep. 26, 2006

(54) THERAPIES USING HEMOPROTEINS

(75) Inventors: Jonathan S. Stamler, Chapel Hill, NC (US); Alfred Hausladen, Durham, NC (US)

(73) Assignee: Duke University, Durham, NC (US)

( * ) Notice: Subject to any disclaimer, the term of this patent is extended or adjusted under 35 U.S.C. 154(b) by 931 days.

(21) Appl. No.: 09/756,478

(22) Filed: Jan. 8, 2001

(65) Prior Publication Data

US 2001/0031727 A1  Oct. 18, 2001

Related U.S. Application Data

(63) Continuation of application No. PCT/US99/15487, filed on Jul. 9, 1999.

(60) Provisional application No. 60/092,372, filed on Jul. 10, 1998.

(51) Int. Cl.
*A61K 38/16* (2006.01)
*A61K 38/00* (2006.01)

(52) U.S. Cl. .............. 514/6; 514/6; 514/16; 514/343; 530/362; 530/363; 530/385

(58) Field of Classification Search ............... 514/2, 514/16, 519, 546, 6, 343; 436/66; 530/385, 530/362, 363
See application file for complete search history.

(56) References Cited

U.S. PATENT DOCUMENTS 5,449,688 A   9/1995  Wahl et al. ............. 514/546
6,297,281 B1  10/2001 Chabrier de Lassauniere et al.

FOREIGN PATENT DOCUMENTS

WO   WO 98/08653   3/1998

OTHER PUBLICATIONS

Gura T., Science 1997 vol. 278, pp. 1041-1042.*
Poole et al., Proc. R. Soc. Lond. B (1994) vol. 255, pp. 251-258.*
Minning, D. et al. "*Ascaris* haemoglobin is a nitric oxide activated 'deoxygenase'," *Nature* 401:497-502 (1999).
Chinje, E. and Stratford, I. "Role of nitric oxide in growth of solid tumors: a balancing act," *Essays Biochem.*, 32:61-72 (1997).
Crawford, M. and Goldberg, D. "Role for the *Salmonella* Flavohemoglobin in Protection from Nitric Oxide," *J. Biol. Chem.*, 273:12543-12547 (1998).
Gardner, P. et al., "Nitric oxide dioxygenase: An enzymic function for flavohemoglobin," *Proc. Natl. Acad. Sci. USA*, 95:10378-10383 (1998).
Hausladen, A. et al., "Nitrosative stress: Metabolic pathway involving flavohemoglobin," *Proc. Natl. Acad. Sci. USA*, 95:14100-14105 (1998).
Kloek, A. et al., "The Tyrosine B10 Hydroxyl Is Crucial for Oxygen Avidity of *Ascaris* Hemoglobin," *Journ. Biol. Chem.*, 269:2377-2379 (1994).

Membrillo-Hernández, J. et al., "The flavohaemoglobin (HMP) of *Escherichia coli* generates superoxide in vitro and causes oxidative stress in vivo," *FEBS*, 32:141-144 (1996).
Poole, Robert. "Oxygen reactions with bacterial oxidases and globins: binding, reduction and regulation," *Antonie Leeuwenhuek*, 65:289-310 (1994).
Poole, Robert, et al., "Reactions of the *Escherichia coli* flavohaemoglobin (Hmp) with oxygen and reduced nicotinamide adenine dinucleotide: evidence for oxygen switching of flavin oxidoreduction and a mechanism for oxygen sensing", *Proc. R. Soc. Lond.*, 255:251-258 (1994).
Thomsen, L.L., et al., "Role of nitric oxide in tumour progression: Lessons from human tumours", *Cancer and Metastasis Reviews*, 17:107-118 (1998).
Tozer, G.M., et al., "Nitric Oxide in Tumour Biology and Cancer Therapy. Part 2: Therapeutic Implications", *Clinical Oncology*, 9:357-364 (1997).
Wennmalm, A., et al., "Dependence of the metabolism of nitric oxide (NO) in healthy human whole blood on the oxygenation of its red cell haemoglobin", *Br. J. Pharmacol.*, 106:507-508 (1992).

* cited by examiner

*Primary Examiner*—B. Dell Chism
(74) *Attorney, Agent, or Firm*—Hamilton, Brook, Smith & Reynolds, P.C.

(57) ABSTRACT

Herein it is shown that hemoproteins (e.g., *Ascaris* hemoglobin, myoglobin, flavohemoglobins) have NO-consuming and deoxygenase activities. The invention provides a method of reducing the concentration of oxygen and/or nitric oxide in a mammal. The method of the invention comprises administering a therapeutically effective amount of a hemoprotein having NO-activated deoxygenase activity or an enzymatically active fragment thereof to a mammal. The method can be used to treat a mammal having pathologically proliferating cells, such as a tumor. In one embodiment, the hemoprotein is administered to reduce the oxygen concentration of a tumor. In another embodiment, the hemoprotein is administered together with a cytotoxic agent to treat a mammal having a tumor. The invention also provides a method of enzymatically generating toxic reactive oxygen species in a mammal for therapeutic purposes. The method comprises administering a therapeutically effective amount of a hemoprotein to a mammal. The invention also provides a composition comprising a hemoprotein having deoxygenase activity or an enzymatically active fragment thereof and a physiologically acceptable carrier. In one embodiment, the composition further comprises a cytotoxic agent and/or a reducing agent. The invention further provides a method of treating a mammal infected with *Ascaris* sp., comprising administering to said mammal a therapeutically effective amount of an inhibitor of NO synthase. The NO-consuming activity of a hemoprotein (e.g., a flavohemoglobin) can be used in a treatment where constriction of blood vessels is desirable, or where it is otherwise desirable to reduce NO concentration, as in inflammation.

3 Claims, 35 Drawing Sheets

SEQUENCE LISTING

```
<160> NUMBER OF SEQ ID NOS: 3

<210> SEQ ID NO 1
<211> LENGTH: 48
<212> TYPE: DNA
<213> ORGANISM: Artificial Sequence
<220> FEATURE:
<223> OTHER INFORMATION: PCR primer

<400> SEQUENCE: 1
gcatccatgg cgaataaaac gagagaacta tccatgaaat cactcgaa                48

<210> SEQ ID NO 2
```

```
<211> LENGTH: 21
<212> TYPE: DNA
<213> ORGANISM: Artificial Sequence
<220> FEATURE:
<223> OTHER INFORMATION: PCR primer

<400> SEQUENCE: 2
ctcttggcaa gccacgttct t                                      21

<210> SEQ ID NO 3
<211> LENGTH: 33
<212> TYPE: DNA
<213> ORGANISM: Artificial Sequence
<220> FEATURE:
<223> OTHER INFORMATION: PCR primer

<400> SEQUENCE: 3
gcatgccacg ttctttccgc cacctacgat gac                         33
```

THERAPIES USING HEMOPROTEINS

RELATED APPLICATIONS

This application is a continuation of International Application No. PCT/US99/15487, which designated the United States and was filed on Jul. 9, 1999, published in English, which claims the benefit of U.S. Provisional Application No. 60/092,372, filed on Jul. 10, 1998. The entire teachings of the above application are incorporated herein by reference.

GOVERNMENT SUPPORT

The invention was supported, in whole or in part, by a grants HL52529 and HL59130 from National Institutes of Health. The Government has certain rights in the invention.

BACKGROUND OF THE INVENTION

Hemoproteins are a group of proteins which contain a heme prosthetic group. They include cytochromes and hemoglobins. These proteins play a critical role in the bioenergetics of aerobic metabolism in mammals, and individuals with mutations or deficiencies in these proteins can have deficiencies in oxygen delivery (e.g., sickle cell anemia) and electron transport (e.g., Leigh syndrome) which are associated with high rates of mortality. Indeed, the importance of balanced oxygen delivery and consumption to ensure normal metabolism (e.g., oxidative phosphorylation) and avoid oxidative stress is well established.

In certain circumstances it can be desirable to modulate (i.e., increase or decrease) the quantity of oxygen in a mammal, either systemically or locally (e.g., in an organ or portion thereof, tissue, cells). For example, appropriate modulation of oxygen levels can be therapeutically beneficial for individuals with anemia or oxidative stress, or in individuals to be treated by local oxygen starvation at the site of a tumor. Thus, a need exists for methods to modulate the concentration of oxygen in a mammal.

When macrophages are activated by bacteria, bacterial products, T lymphocyte-derived cytokines, and antigens, they respond by converting arginine into NO via nitric oxide synthase. Blocking the synthetic pathway of NO production has been demonstrated to alleviate immunologically mediated joint destruction that occurs in animal models of arthritis, as well as in glomerulonephritis (McCartney-Francis, N. et al., *J. Exp. Med.* 178:749–754 (1993); Weinberg, J. B. et al., *J. Exp. Med.* 179:651–660 (1994)). NO is also thought to play a role in other inflammatory conditions such as colitis, iritis and hemodynamic shock. In addition, tumor cells secrete NO to regulate blood flow. Thus, methods of therapy to reduce the concentration of NO are desirable to alleviate these conditions.

SUMMARY OF THE INVENTION

The invention relates to the NO consuming and $O_2$ consuming activity of naturally occurring and variant hemoproteins also referred to herein as deoxygenases or hemoproteins having deoxygenase activity (also, hemoproteins having NO-consuming activity). Hemoproteins can be identified as having these enzymatic acitivies by the methods described herein used to characterize enzymatic activities. In particular, the invention relates to the NO-consuming and deoxygenase activity of *Ascaris* hemoglobin (AH), myoglobin and flavohemoglobins (e.g., flavohemoglobins from bacteria, plants, fungi). One or more hemoproteins can be used in a method to reduce the concentration of oxygen in an aqueous solution, by adding to the aqueous solution a hemoprotein having deoxygenase activity, as well as a reducing agent, and incubating the resulting solution under conditions suitable for deoxygenase activity. For NO-enhanced deoxygenase activity, depending on the enzyme, NO or an NO donor can be added to the aqueous solution to enhance deoxygenase activity under appropriate conditions. Hemoproteins can also be used to reduce the concentration of NO in an aqueous solution.

In one aspect, the invention relates to a method of enzymatically reducing the concentration of oxygen and/or NO in a mammal. The method comprises administering a therapeutically effective amount of a hemoprotein with deoxygenase activity to a mammal in need thereof.

In another aspect, the invention relates to a method of treating a mammal having a disorder characterized by the presence of pathologically proliferating cells, such as prostatic hypertrophy, restenosis (as of a coronary artery), psoriasis or a tumor. The method comprises administering a therapeutically effective amount of a hemoprotein with NO-activated deoxygenase activity to a mammal having such a condition. In additional embodiments, the invention relates to methods of treating a mammal having a tumor. In one embodiment, the invention relates to a method of deoxygenating a tumor. The method comprises administering a therapeutically effective amount of a hemoprotein with deoxygenase activity to a mammal having a tumor. In another embodiment, the invention relates to a method of anti-tumor therapy. The method comprises administering a therapeutically effective amount of a hemoprotein with deoxygenase activity and a therapeutically effective amount of a cytotoxic agent to a mammal having a tumor. In a particular embodiment, the cytotoxic agent is a bioreductive cytotoxic agent and the deoxygenase can be one that is activated by NO. In another embodiment, the invention is a method of potentiating the cytotoxic activity of a bioreductive cytotoxic agent. The method comprises administering a therapeutically effective amount of a hemoprotein with NO-activated deoxygenase activity and a therapeutically effective amount of a bioreductive cytotoxic agent to a mammal having a tumor.

In another aspect, the invention relates to a method of enzymatically generating toxic reactive oxygen species (e.g., hydrogen peroxide, superoxide, hydroxyl) for therapeutic purposes (e.g., a toxic effect in a tumor). The method comprises administering an effective amount of a hemoprotein (e.g., a globin with deoxygenase activity) to a mammal in need of such therapy.

In another aspect, the invention relates to a composition comprising a hemoprotein having NO-activated deoxygenase activity and a physiologically acceptable carrier. In one embodiment, the composition further comprises a cytotoxic agent (e.g., an anti-tumor agent) and/or a reducing agent. In a preferred embodiment, the cytotoxic agent is a bioreductive cytotoxic agent.

In another aspect, the invention relates to a method of reducing the concentration of oxygen in an aqueous solution, comprising adding a hemoprotein having NO-activated deoxygenase activity to the solution. Preferably, the solution contains NO, or NO is added to the solution either directly or indirectly.

In another aspect, the invention relates to a method of designing an oxygen lowering enzyme.

The invention further relates to naturally occurring and mutant hemoproteins with NO-activated deoxygenase activity, as described herein, for use in therapy (including prophylaxis) or diagnosis, and to the use of such naturally occurring, mutant or variant hemoproteins, or active fragments of any of the foregoing, with NO-activated deoxygenase activity for the manufacture of a medicament for the treatment of a particular disease or condition as described herein (e.g., cancer, Ascaris sp. infection, prostatic hypertrophy, restenosis).

In a further aspect, the invention relates to a method of treating a mammal infected with a microbe or parasite which uses an enzymatic hemoprotein to regulate oxygen tension. In one embodiment, the invention relates to a method of treating a mammal infected with a nematode of the genus Ascaris. The method comprises administering a therapeutically effective amount of an inhibitor of NO synthase to the infected mammal. The invention further relates to NO synthase inhibitors for use in therapy (including prophylaxis) or diagnosis of microbial or parasitic infection (e.g., Ascaris sp. infection), and to the use of NO synthase inhibitors for the manufacture of a medicament for the treatment of microbial or parasitic infection (e.g., Ascaris sp. infection).

Described herein are compositions comprising hemoproteins, for example, flavohemoglobins, for pharmaceutical use in methods of reducing NO concentrations, for example, for the treatment of inflammatory conditions or tumors in mammals. Flavohemoglobins to be incorporated into a pharmaceutical composition can be isolated from various species of bacteria such as E. coli, from yeast such as Saccharomyces cerevisiae, from plants, or can be recombinantly made in a host organism, for example. Antitumor therapy can be carried out by introduction (e.g., by infusion) into the tumor of a hemoprotein (e.g., flavohemoglobin or a suitable composition comprising flavohemoglobin) at the site of the tumor, for example, which causes constriction of blood vessels and reduction of blood flow in tumors. Anti-inflammatory therapy can be carried out by local or systemic administration of a composition comprising a hemoprotein having NO-consuming activity, as appropriate, depending on the disease or medical disorder to be alleviated by the therapy.

resulted in a reduced NO signal (2.0 nAmps) and an increased rate of decay. Specifically, complete decay was seen within one min, compared to greater than 10 min in the absence of AH or NADPH.

Figure 2A:
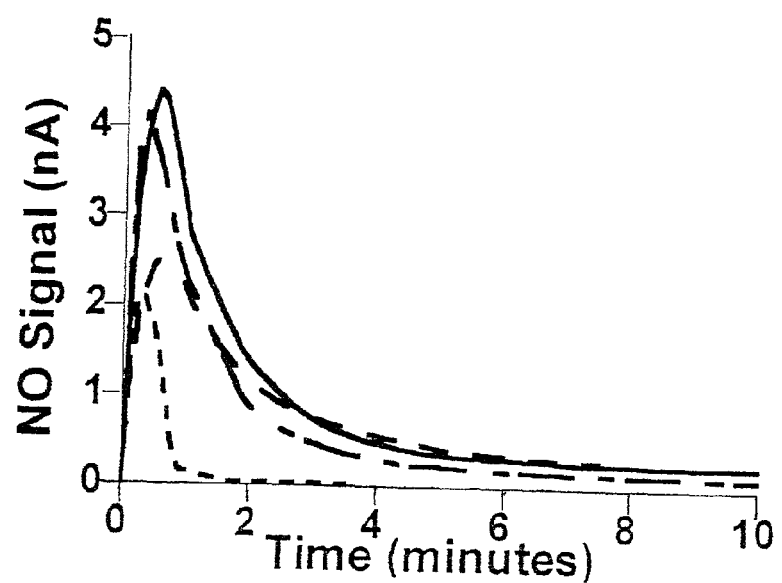
FIG. 2A is a graph showing that AH consumes NO. An NO electrode was used to measure the consumption of 6 µM NO. NO added to buffer alone (PBS, pH 6) (solid line), resulted in a peak height of 4.4 nA that slowly decayed. NO added to buffer plus 500 µM NADPH (short-long dashed line) yielded an NO signal (4.2 nAmps peak height) that decayed at a comparable rate to NO in buffer alone. NO added to AH (1.5 µM heme content) in the absence of NADPH (long dashed line) resulted in a reduced peak of 2.5 nA, consistent with reaction of NO with heme-bound oxygen. Decay of the NO signal, however, displayed similar kinetics to NO in the absence of AH. NO added to AH (1.5 µM heme content) plus 500 µM NADPH (short dashed line)
Figure 2B:
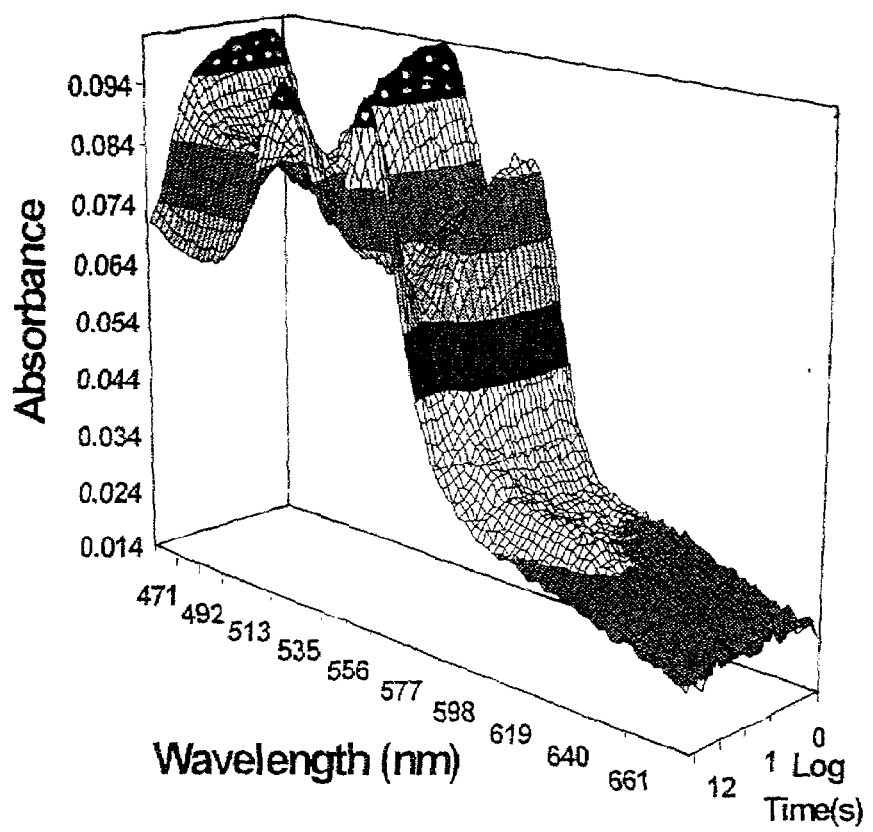

FIG. 2B is a three dimensional composite of the visible spectrum showing the kinetics of AH interaction with NO in the absence of NADPH. AH(FeII)$O_2$ (6 μM heme) was mixed with diethylamine NONOate (DEANO) (25 μM) in a stopped-flow spectrophotometer. Before mixing, all solutions were deoxygenated by bubbling with argon gas for 45 minutes. Every twentieth spectrum of all spectra collected for 50 seconds is shown, demonstrating the loss of the starting AH(FeIII)NO.

Figure 2C:
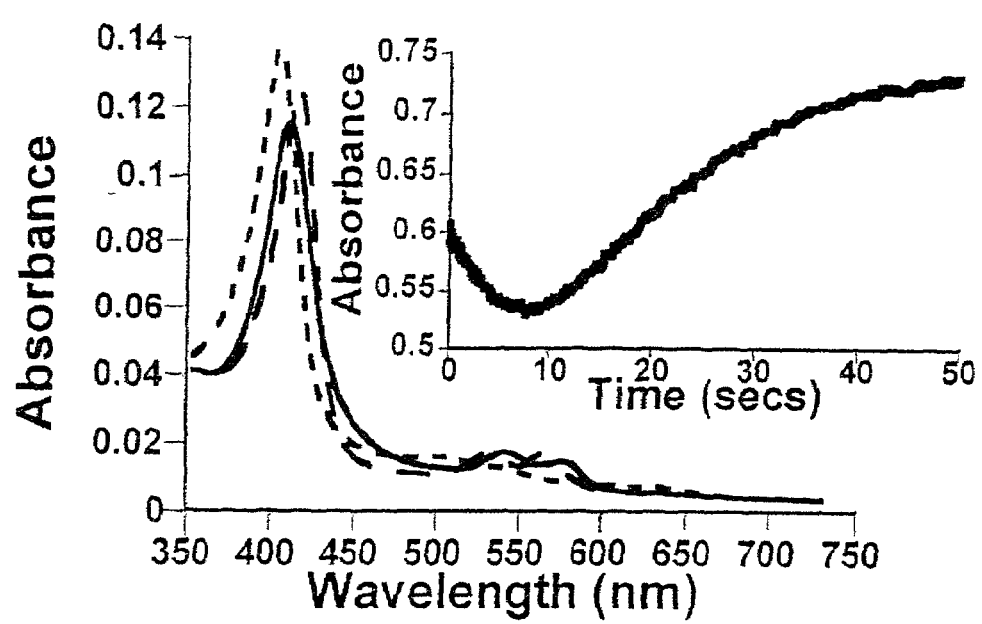

FIG. 2C shows modeled spectra for the kinetics of AH interaction with NO in the absence of NADPH (shown in FIG. 2B). Using Pro-K (Applied Photophysics) to calculate predicted spectra, the algorithm that best fit the data was A (starting spectrum)+B (unabsorbant species, NO) goes to D (final spectrum). After addition of NO, the starting spectrum of AH(FeIII)$O_2$ (solid line) is converted to a modeled intermediate spectrum which resembles AH(FeIII) (short dashed line), followed by a final spectrum corresponding to AH(FeIII)NO (long dashed line). Inset: Spectral changes at 418 nm. Upon addition of NO, absorbance at 418 nm rapidly decreases (within 8 sec.) from 0.6 to 0.53, due to the formation of the AH(FeIII) intermediate. The subsequent rise in absorbance is due to the buildup of AH(FeIII)NO.

Figure 2D:
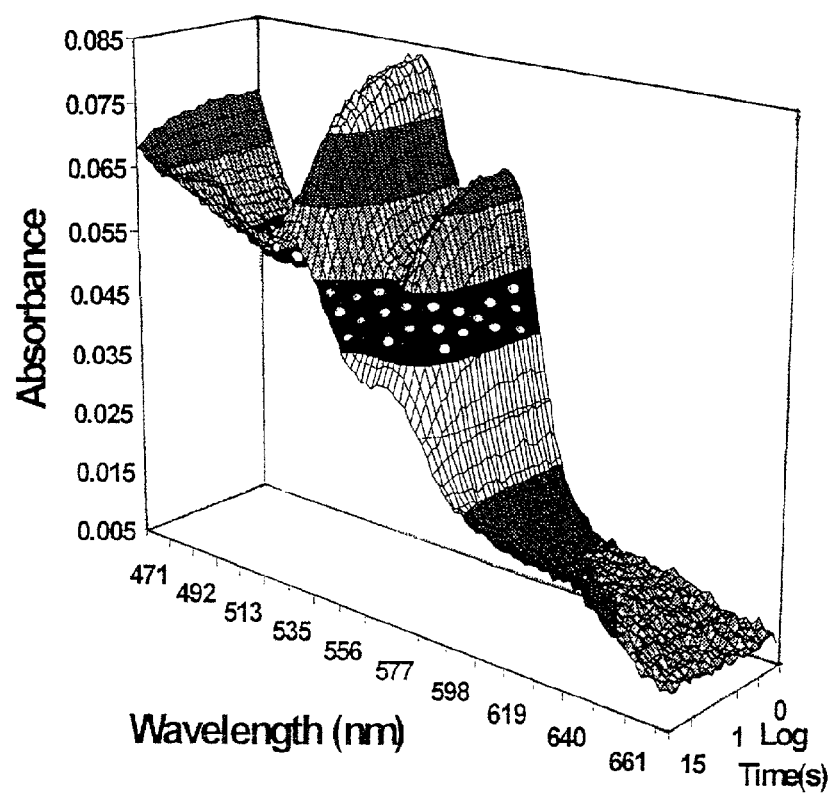

FIG. 2D is a three dimensional composite of the visible spectrum showing the kinetics of AH interaction with NO in the presence of NADPH. AH(FeH)$O_2$ (6 μM heme) was mixed with 25 μM diethylamine NONOate (DEANO) plus 500 μM NADPH (final concentration) under low oxygen tension. Every twentieth spectrum of all spectra collected for 50 seconds is shown, demonstrating the loss of the starting AH(FeII)$O_2$ spectrum, due to oxidation to form AH(FeIII). No AH(FeIII)NO is detected in the final spectrum.

Figure 2E:
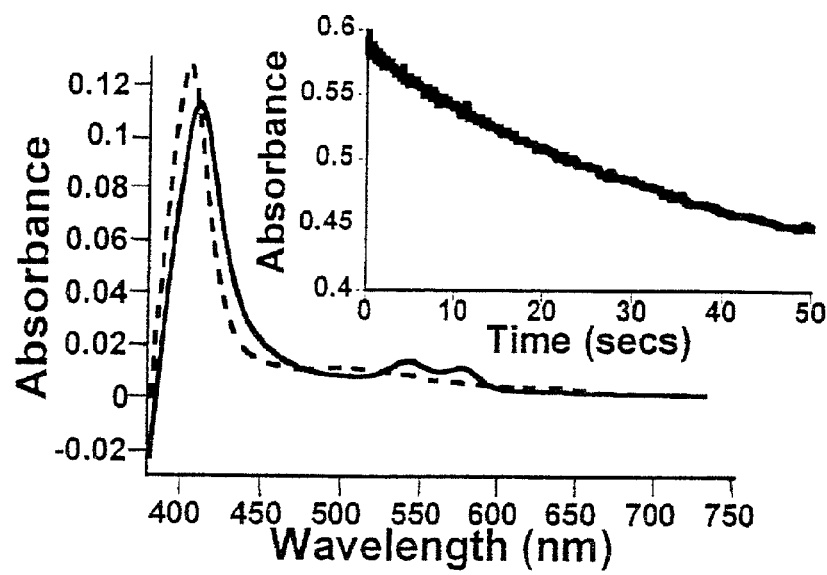

FIG. 2E shows modeled spectra for the kinetics of AH interaction with NO in the presence of NADPH (shown in FIG. 2D). Predicted spectra were calculated as described in FIG. 2C. The algorithm that best fit the data was A (starting spectrum)+B (unabsorbant species, NO) goes to C (final spectrum). After mixing with NO, the starting spectrum of AH(FeIII)$O_2$ (solid line) is converted to a final spectrum which resembles AH(FeIII) (short dashed line). (The inset shows spectral changes at 418 nm.) Upon addition of NO, absorbance at 418 nm slowly decreases over 50 sec from 0.6 to 0.45, compared to the rapid change from 0.6 to 0.53 in the absence of NADPH, suggesting that AH(FeIII) competes with AH(FeII)$O_2$ for NO.

Figure 2F:
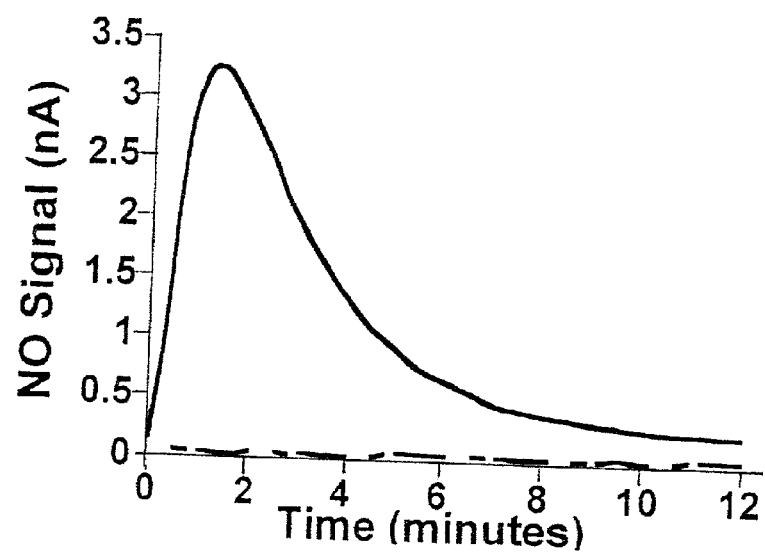

FIG. 2F is a graph showing AH metabolism of NO released by DEANO. DEANO (5 μM final concentration) was added to a solution containing 500 μM NADPH (solid line) and NO was measured electrochemically (peak NO 3.2 nA). Similar addition of DEANO (5 μM) in the presence of AH (1.5 μM heme content) and 500 μM NADPH caused no visible deflections (short-long dashed line), demonstrating efficient metabolism of NO.

Figure 3A:
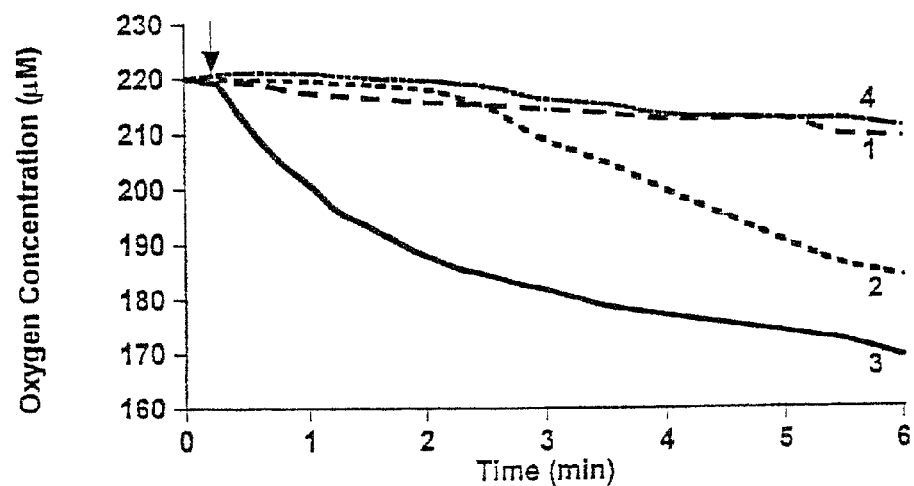

FIG. 3A is a graph showing oxygen consumption by AH. A Clark electrode was placed in a sealed glass vessel for oxygen measurements. Addition of NO (7.5 μM) to the vessel produced minimal reduction in oxygen tension (long dashed line, 1). Addition of 500 μM NADPH to buffer containing AH (0.43 μM) resulted in oxygen consumption following a 2.5 min lag phase, suggesting an autocatalytic process (short dashed line, 2). NO (7.5 μM) added to buffer containing both AH (0.43 μM) and NADPH (500 μM) resulted in immediate rapid consumption of oxygen (sold line, 3) whereas no oxygen was consumed in the absence of NADPH (dotted line, 4). Importantly, the addition of AH at a later time (2.5 min) did not increase oxygen consumption in 4. The arrow indicates the time of NO addition in lines 1, 3 and 4 and the time of addition of NADPH for line 2. Data are representative of three similar experiments.

Figure 3B:
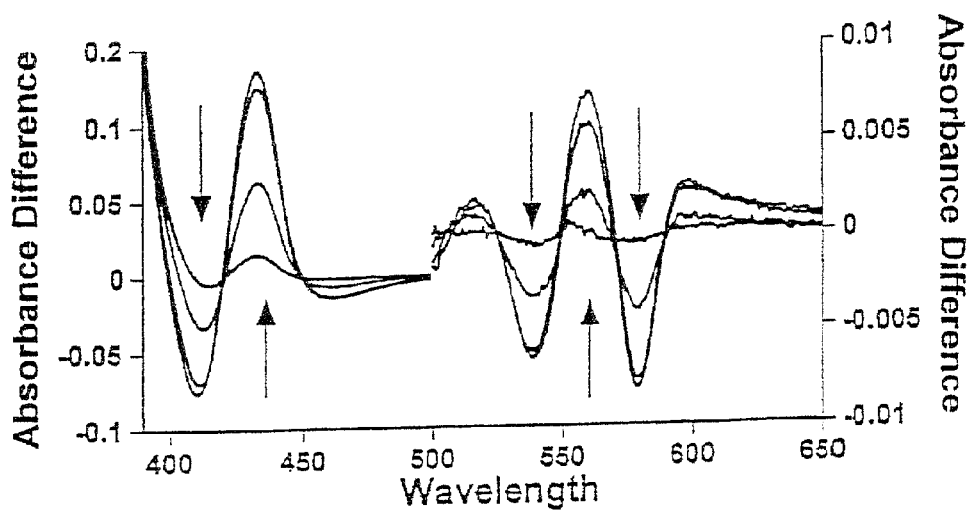

FIG. 3B is a graph showing NADPH mediated deoxygenation of AH. A solution of AH (PBS, pH 6.0) was deoxygenated by bubbling with argon for 45 min (initial spectrum). 500 μM NADPH was then added, and the spectral change to an unliganded Fe(II) (deoxy) form was followed over 10 min. Spectra are shown as differences versus the pre NADPH addition spectrum.

Figure 4:
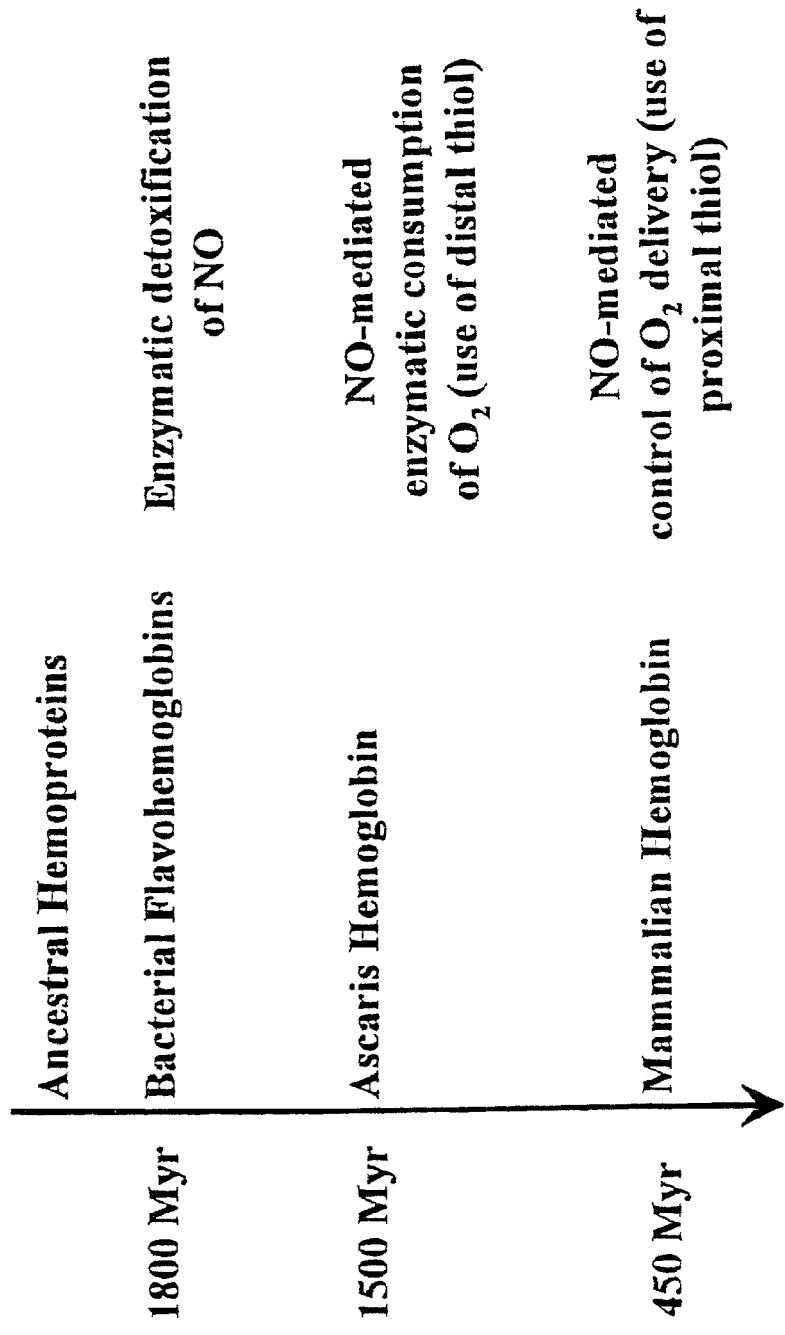

FIG. 4 is a diagram of a scheme for evolution of hemoglobins rationalized by NO-related functions. The diagram shows the position of nematode hemoglobins at the divide between bacteria and higher animals (Sherman, D. R., et al., Proc. Natl. Acad. Sci. USA 89:11696–11700 (1992)), and the transformation of a NO detoxification function into a respiratory function. Distal and proximal designate position within the heme pocket. Myr represents millions of years ago.

Figure 5A:
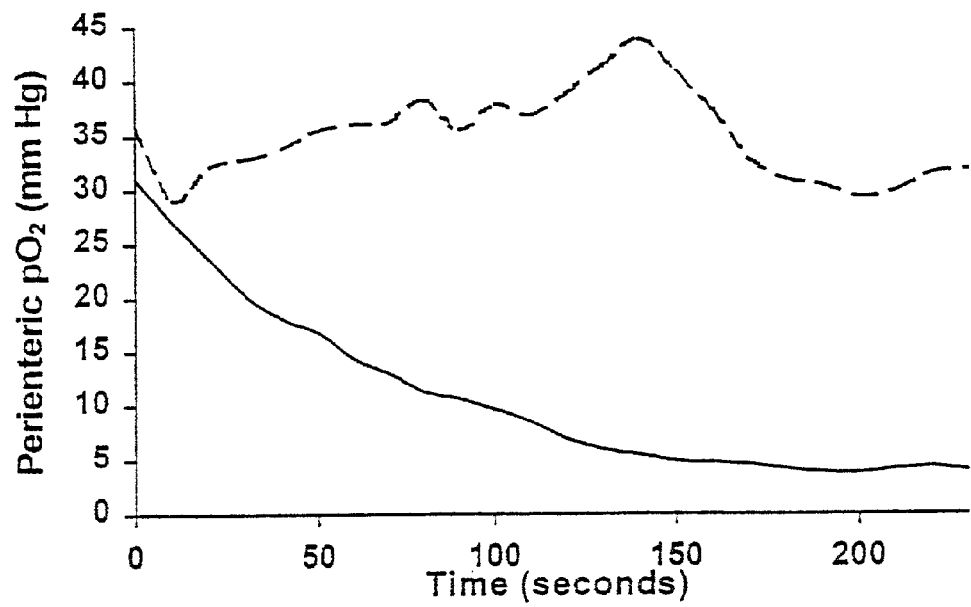

FIG. 5A is a graph showing the p$O_2$ of the perienteric cavity in freshly isolated *Ascaris* worms over time. A cannula was inserted into the perienteric space ~1 cm below the head, through which a fiber optic $O_2$ probe was passed. Probe output (p$O_2$) dropped with passage into the cavity to 4 mm Hg (solid line). A second cannula was used to drain the perienteric fluid. The perienteric p$O_2$ was dramatically elevated following complete drainage (dashed line).

Figure 5B:
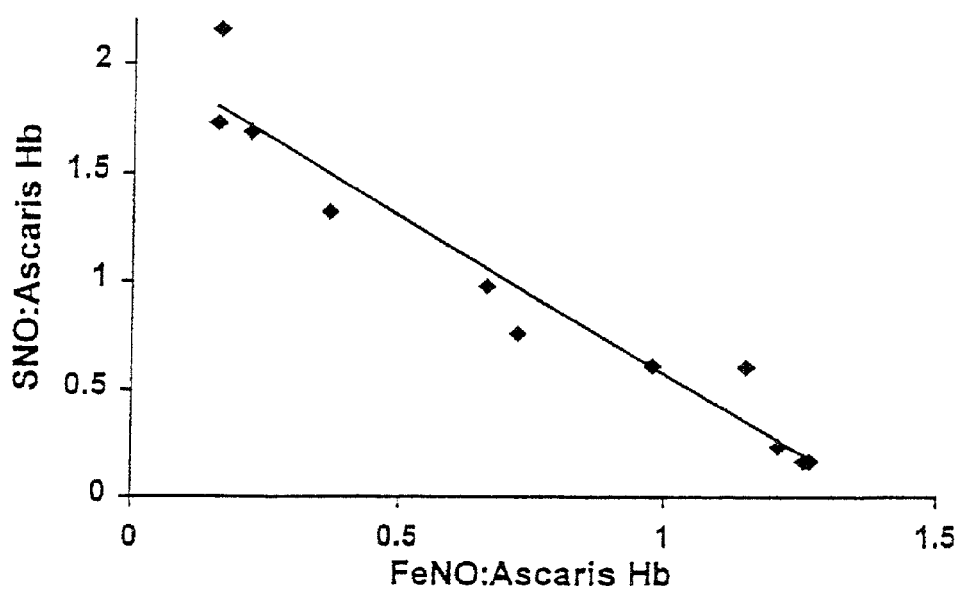

FIG. 5B is a graph showing the inverse relationship between the amount of SNO and the amount of metal nitrosyl (FeNO) in the perienteric fluid of freshly isolated *Ascaris* worms. The perienteric fluid of individual adult female *Ascaris* worms (data points) was collected and analyzed for SNO and FeNO by photolysis-chemiluminescence. Data were normalized to *Ascaris* hemoglobin content of the fluid.

Figure 6:
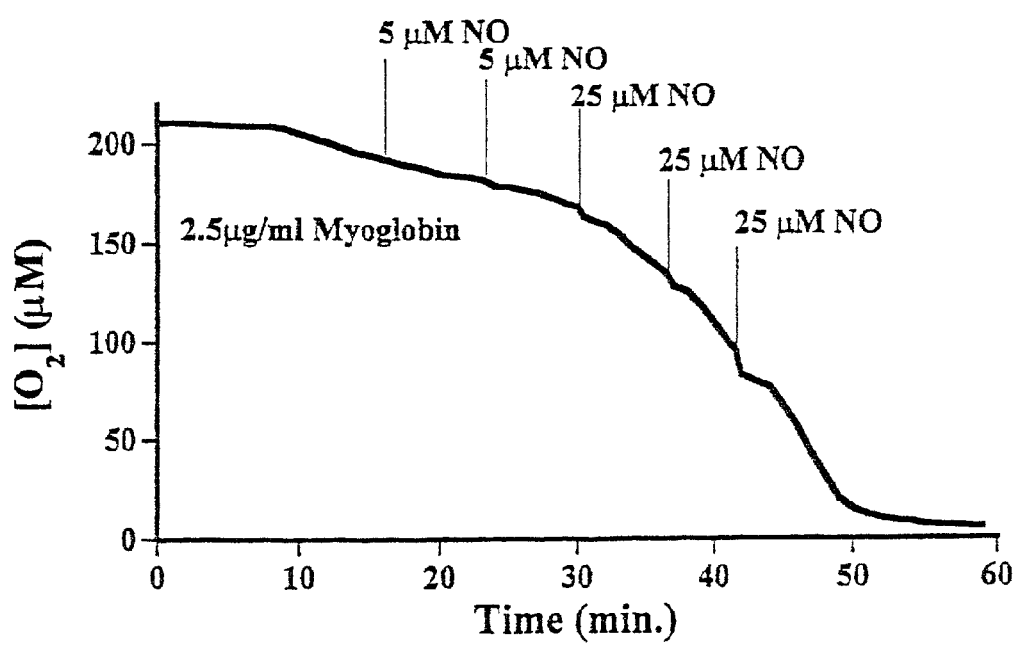

FIG. 6 is a graph of oxygen concentration versus time, showing that myoglobin has a deoxygenase activity which is driven by NO. Myoglobin was added to phosphate buffered saline at a final concentration of 5 μM. Oxygen consumption was initiated by addition of NADPH (nicotinamide adenine dinucleotide phosphate, reduced form) or NADH (nicotinamide adenine dinucleotide, reduced form). Rate of oxygen consumption was accelerated by the addition of 1 to 25 μM NO, which had little effect when added alone.

Figure 7A:
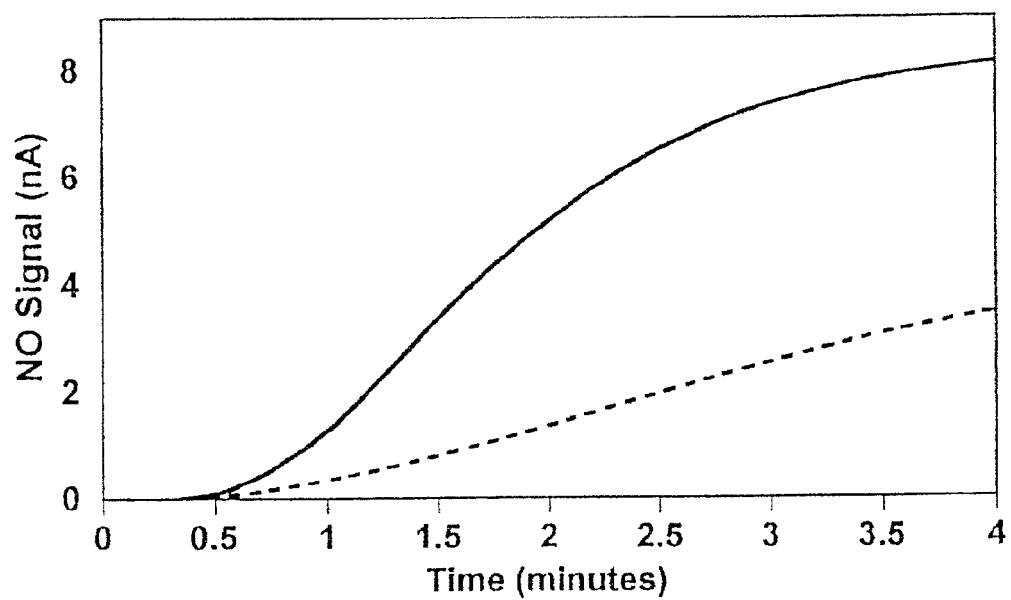

FIG. 7A is a graph showing release of NO from S-nitrosothiols in *E. coli* with time. S-nitrosocysteine (0.1 mM) was added to growth medium (broken line) or a suspension of *E. coli* in growth medium (solid line) and NO release over time was measured by electrode.

Figure 7B:
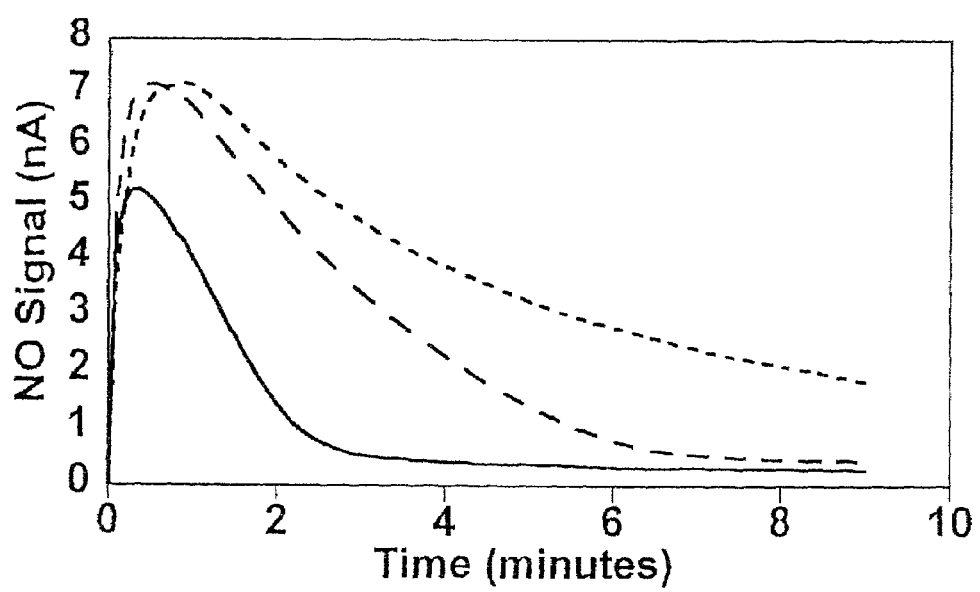

FIG. 7B is a graph of NO in growth medium as measured by electrode, showing that *E. coli* cells consume NO over time in both a constitutive and an inducible manner. A saturated solution of NO was added to growth medium (dotted line) or to a suspension of *E. coli* that had received no treatment (dashed line) or to *E. coli* pretreated with 0.2 mM SNO-Cys (solid line).

Figure 7C:
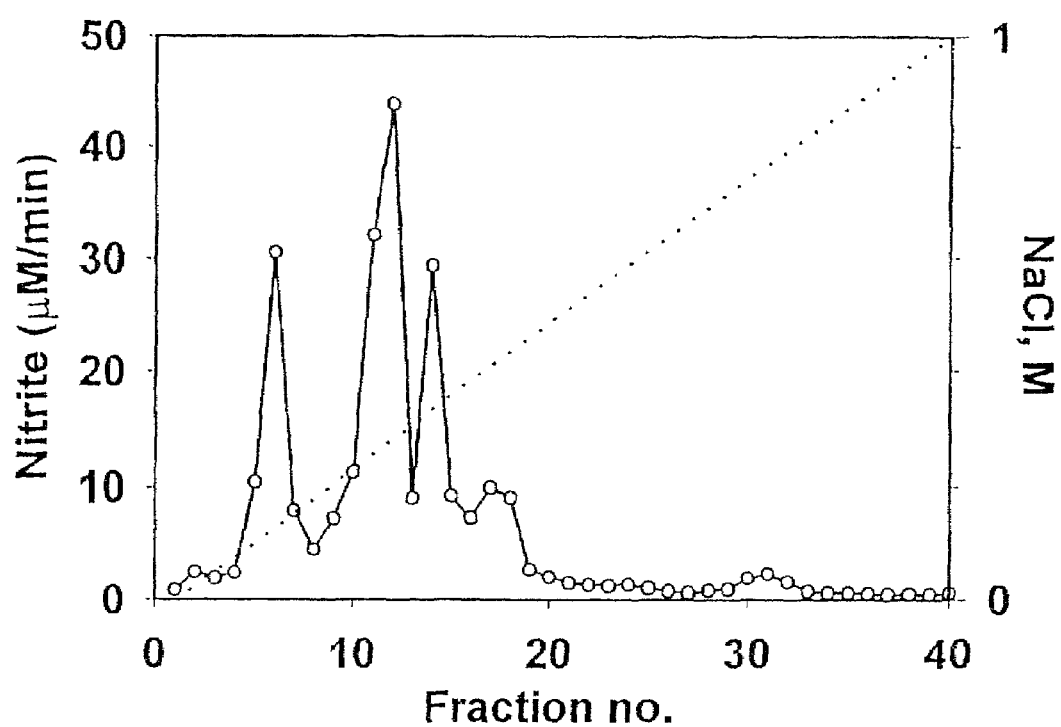

FIG. 7C is a plot of the concentrations of nitrite from 0.5 mM SNO-Cys found in fractions of an ion exchange column used to separate the lyase activities found in an extract of *E. coli* cells.

Figure 7D:
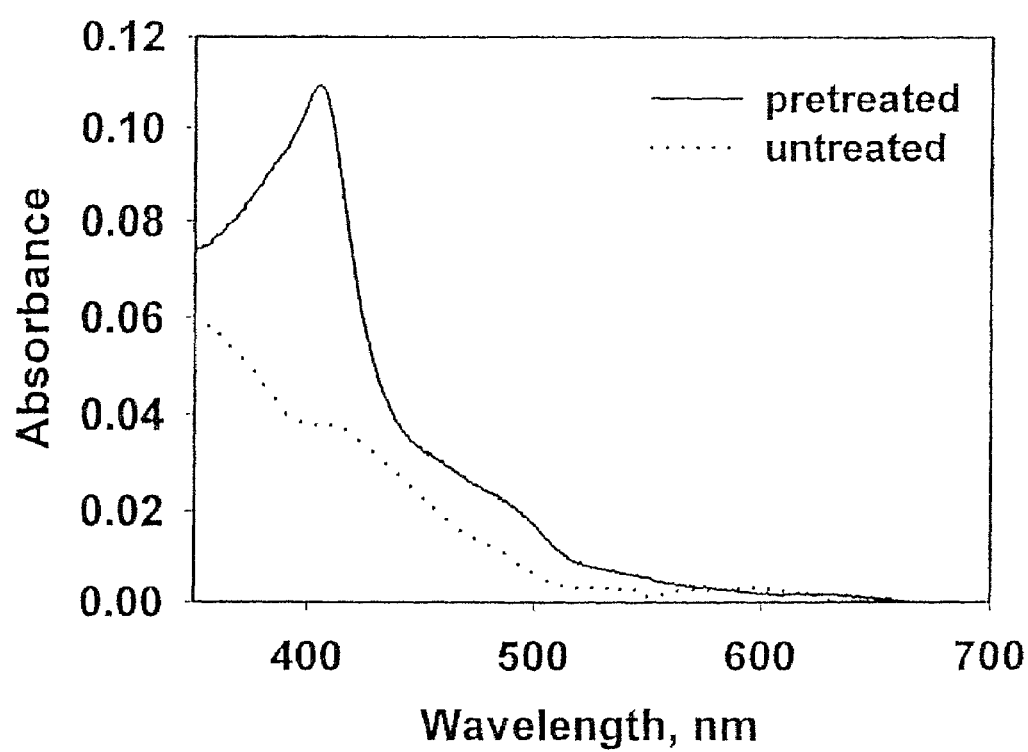

FIG. 7D is a spectrum (absorbance v. wavelength) of column fractions—prepared from untreated (dashed line) or pretreated *E. coli* cells (solid line)—which contain an inducible NADH-dependent NO-metabolizing activity. The spectrum is characteristic of a heme protein.

Figure 8A:
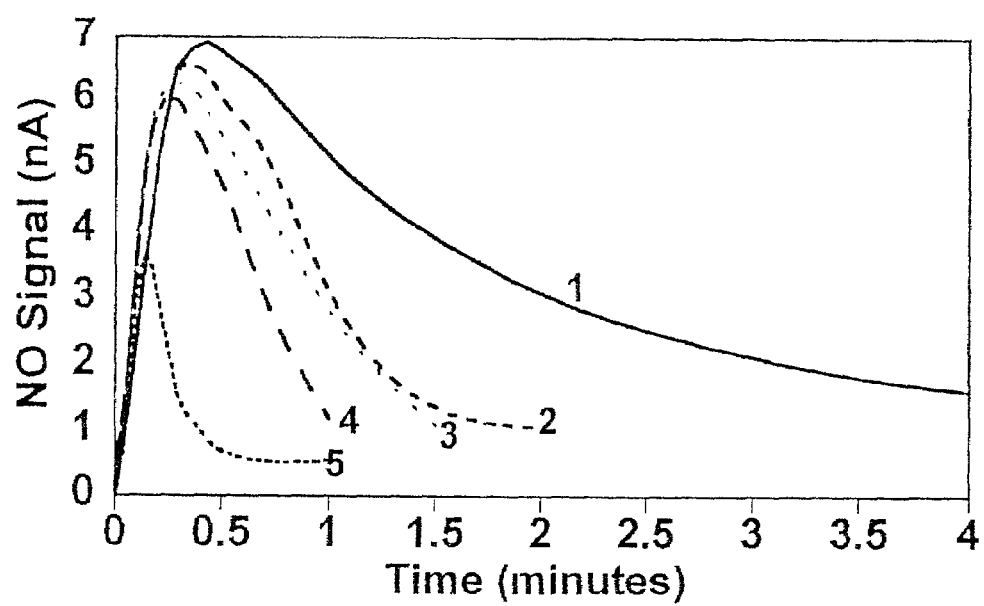

FIG. 8A is a graph of NO assayed from samples of buffer or extracts of Δhmp or wild type E. coli cells after various treatments: addition of 10 μM NO to 20 mM BisTrisPropane, pH 7.0 (line 1), NADH dependent NO consumption by extracts from untreated Δhmp cells (line 2), and SNO-Cys treated (line 3) Δhmp mutant cells, or untreated wild type cells (line 4) and SNO-Cys treated (line 5) wild type cells.

Figure 8B:
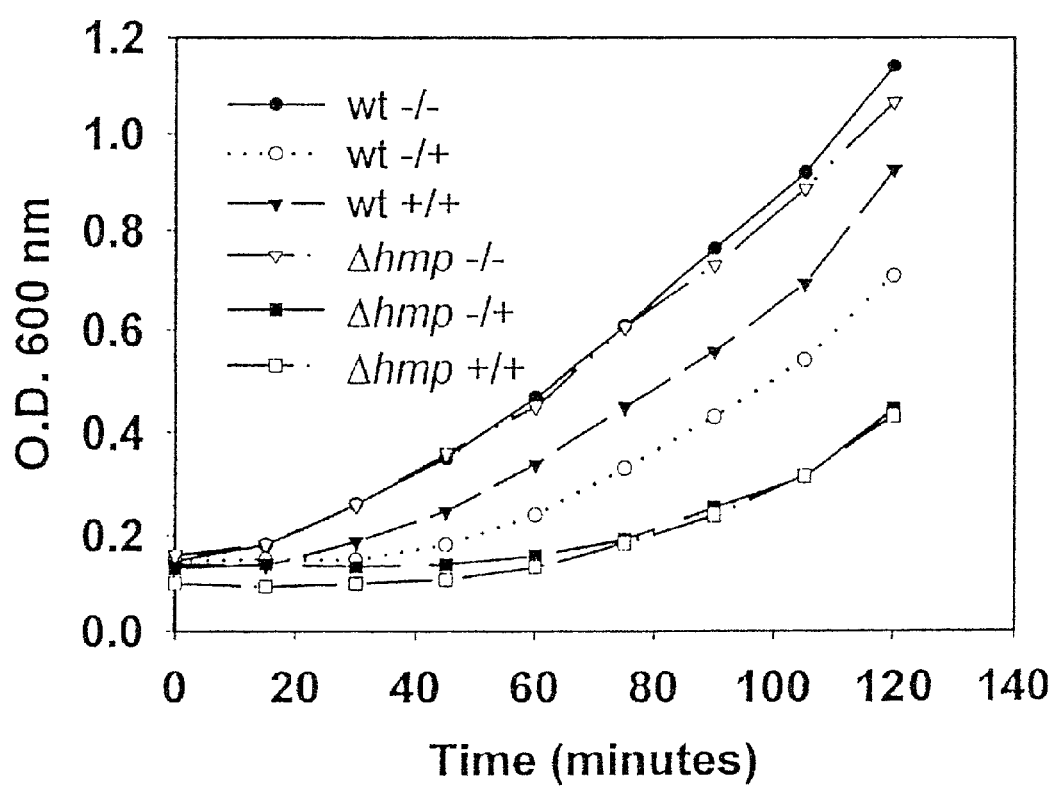

FIG. 8B is a graph showing the growth of E. coli liquid cultures with time, as measured by turbidity of the cultures. Cells which had (+/+) or had not (−/+) been pretreated with 0.2 mM SNO-Cys for 90 minutes were challenged with the same dose at time 0. Control cells were neither pretreated nor challenged with SNO-Cys (−/−). HMP is required for NO consumption and resistance to nitrosative stress.

Figure 9A:
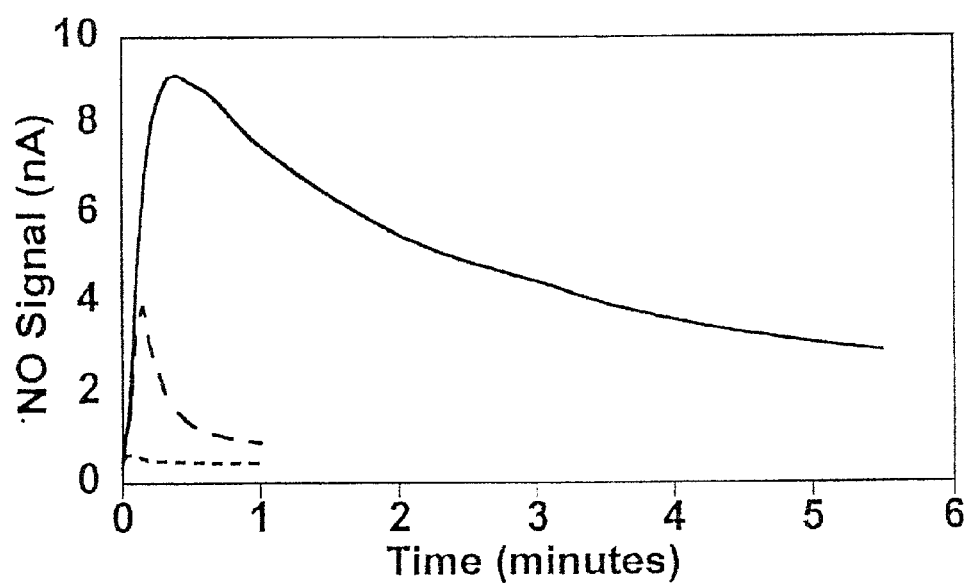

FIG. 9A is a graph showing the NO electrode signal after addition of ~10 μM NO to buffer (solid line) or ~10 μM NO (dotted line) or ~35 μM NO (dashed line) to 40 μg/ml purified HMP+0.1 mM NADH.

Figure 9B:
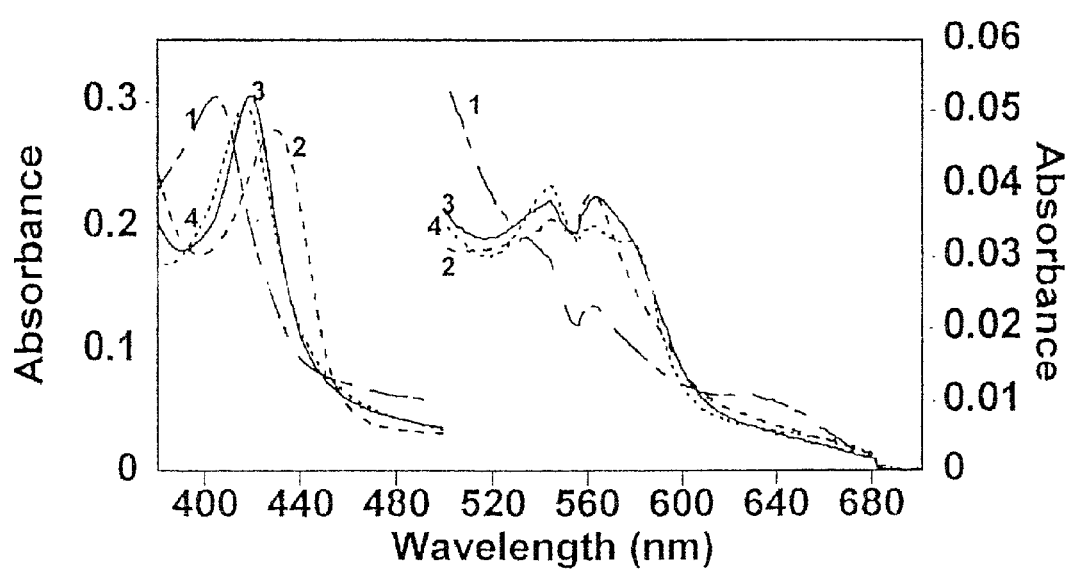

FIG. 9B shows absorption spectra of purified HMP. 450 μg/ml HMP were examined spectrophotemetrically under anaerobic conditions (line 1). Addition of NADH revealed a ferrous iron like spectrum (line 2). Addition of NO saturated solution generated an iron-nitrosyl spectrum (line 3). Air exposure of this iron-nitrosyl (with brief vortexing) resulted in an oxygen bound (ferrous) iron spectrum (line 4).

Figure 9C:
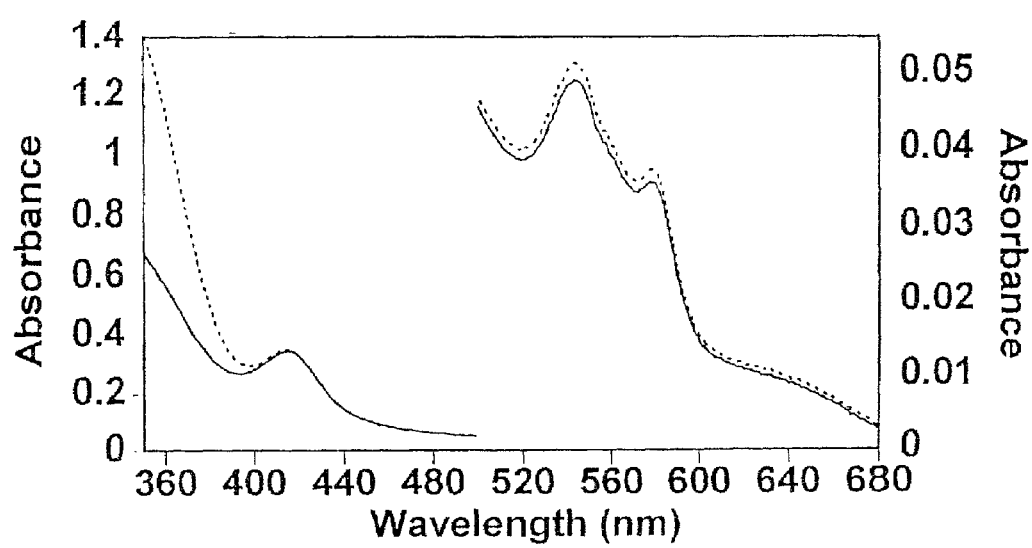

FIG. 9C shows absorption spectra of purified HMP during aerobic turnover of NO in the presence of NADH. 300 μM NADH was added to 400 μg/ml HMP in air (dotted line). Addition of 100 μM NO from a saturated solution resulted in the consumption of NADH but no loss of the oxygen bound ferrous iron spectrum (solid line).

Figure 9D:
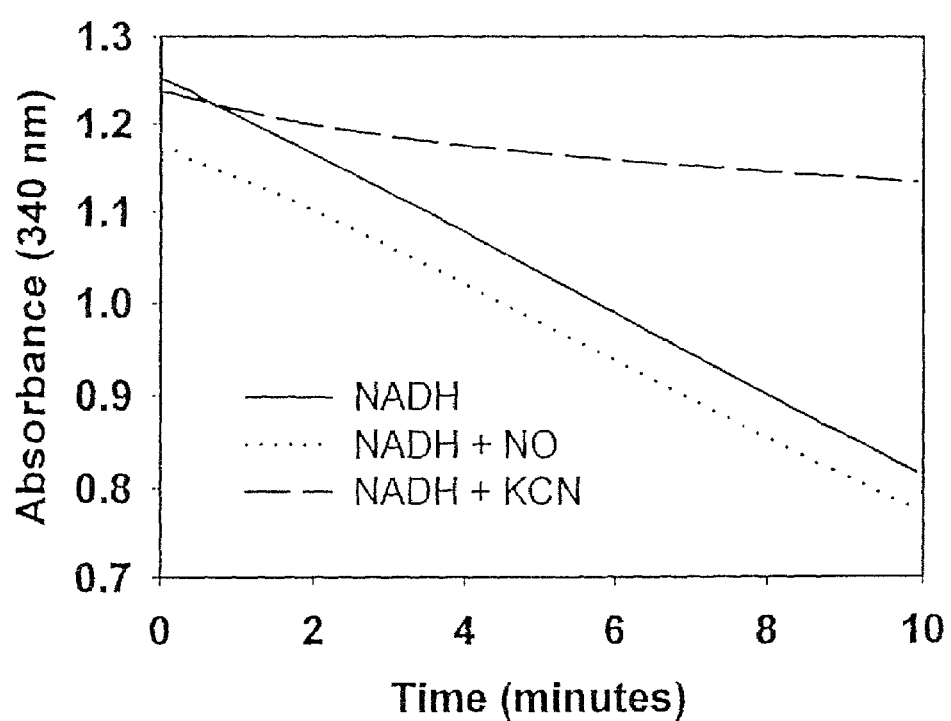

FIG. 9D is a graph of the peak absorbance (at 340 nm) of NADH for purified 20 μg/ml HMP incubated without any further addition (solid line) in the presence of 100 μM added NO (dotted line) or 1 mM added KCN (dashed line). NADH consumption is not increased during NO turnover by HMP and is cyanide inhibitable.

Figure 9E:
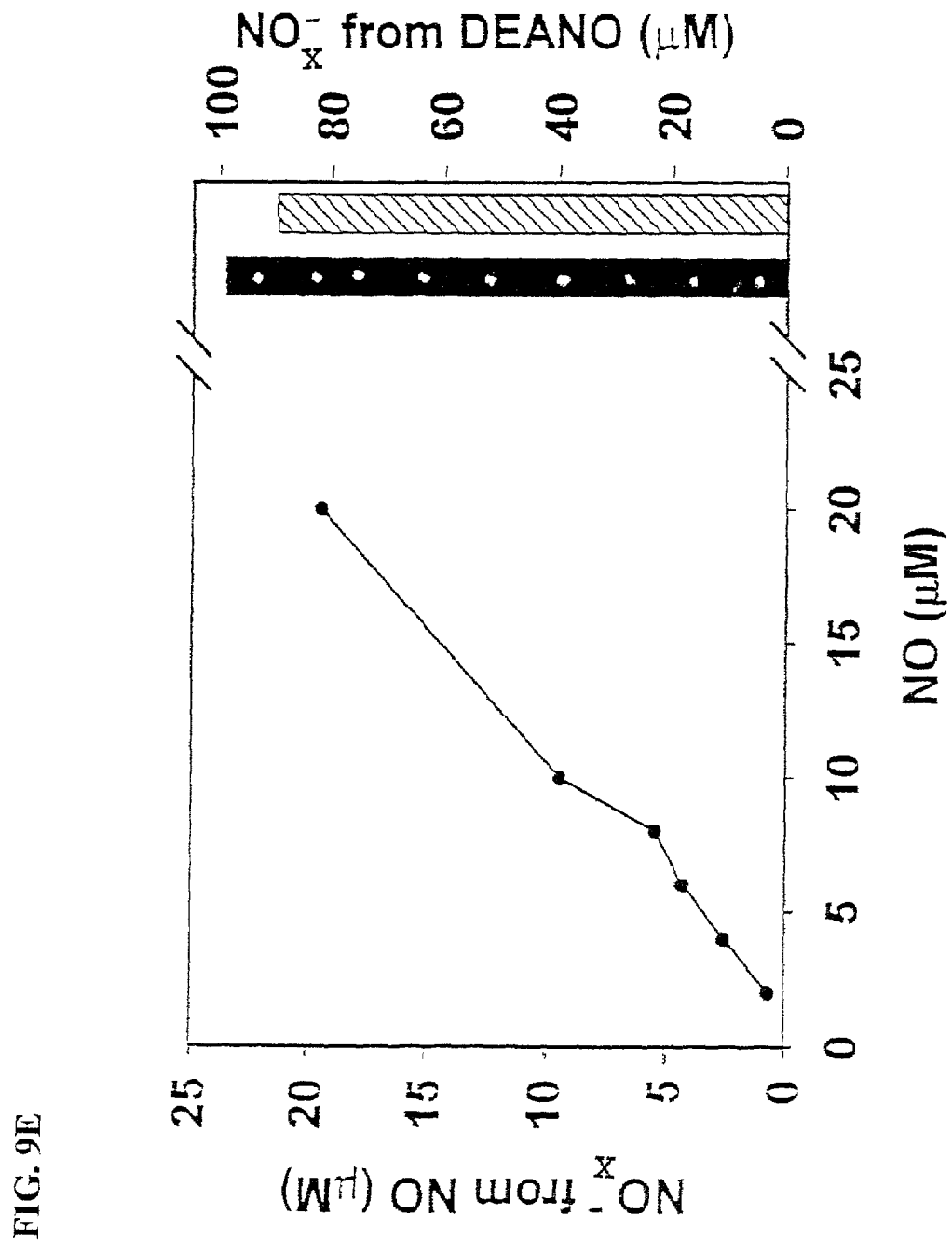

FIG. 9E is a graph demonstrating that nitrite and nitrate are the main products of aerobic NO metabolism by purified HMP. The graph shows nitrite yields after addition of a saturated NO solution to 40 μg/ml HMP in the presence of 0.1 M NADH (solid line) or after autooxidation (filled bar) or HMP oxidation (hatched bar) of NO released from 0.1 mM diethylamine-NO.

Figure 9F:
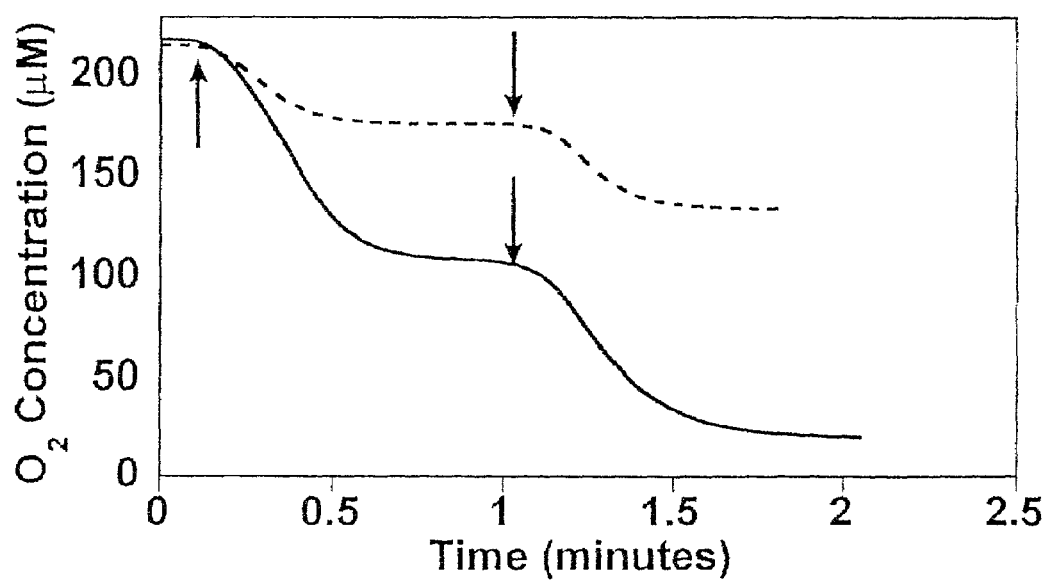

FIG. 9F is a graph illustrating oxygen consumption (by electrode measurements of oxygen concentration over time). NO oxidation by HMP (solid line) increases oxygen consumption 4-fold over NO autooxidation (broken line), i.e., the stoichiometry is 4 NO per $O_2$ in the former case and 1 NO per $O_2$ in the latter. At the times indicated by the arrows, 100 μM NO was added.

Figure 10A:
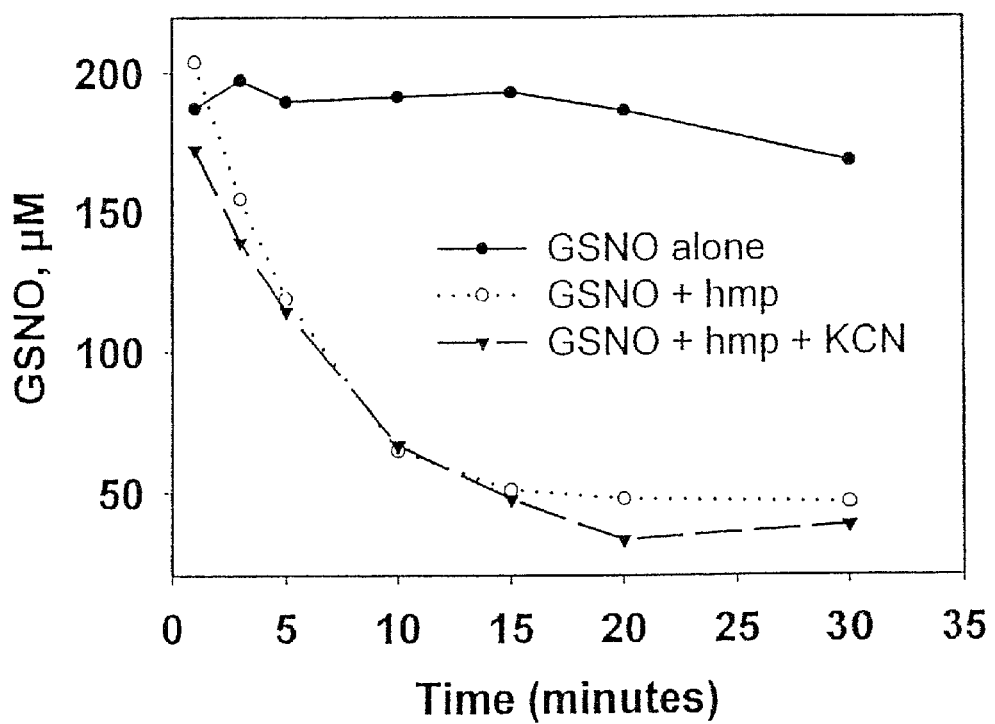

FIG. 10A is a graph of GSNO concentration measured from samples of a reaction of GSNO with purified HMP. Decomposition of 200 μM GSNO was accelerated by 75 μg/ml HMP in the presence of 0.1 mM NADH and was not inhibited by 1 mM cyanide.

Figure 10B:
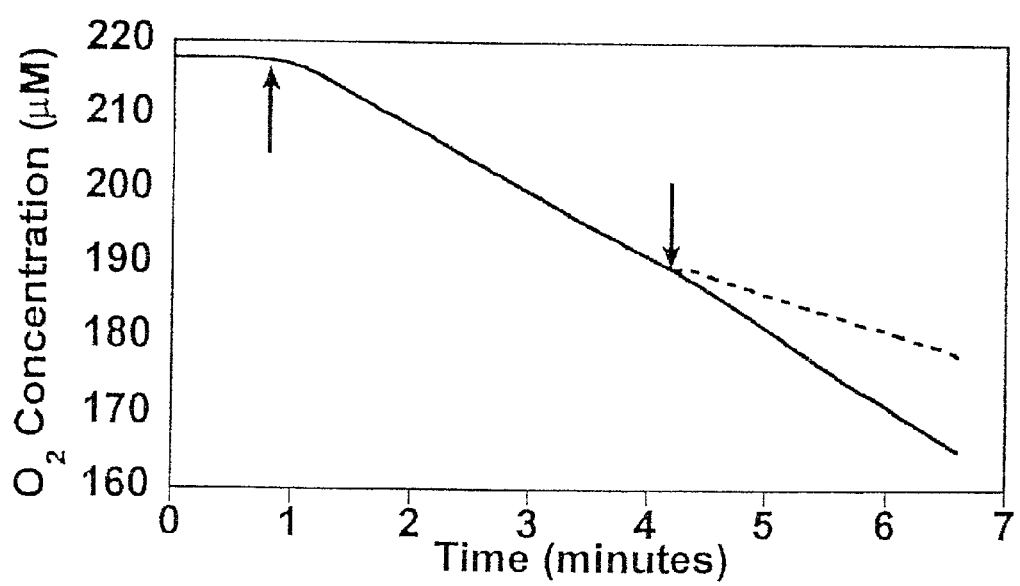

FIG. 10B is a graph of $O_2$ concentration, as measured by electrode over a period of time, showing that GSNO decomposition is oxygen independent. Addition of 0.1 mM NADH, indicated by the first arrow at one minute, increased oxygen consumption by HMP (75 μg/ml). Addition of 0.2 mM GSNO, as indicated by the second arrow (at 4 minutes; solid line), resulted in a minimal change in oxygen consumption. Addition of 0.2 mM GSNO and 1 mM cyanide, as indicated by the second arrow (at 4 minutes; dashed line), reduced oxygen consumption.

Figure 10C:
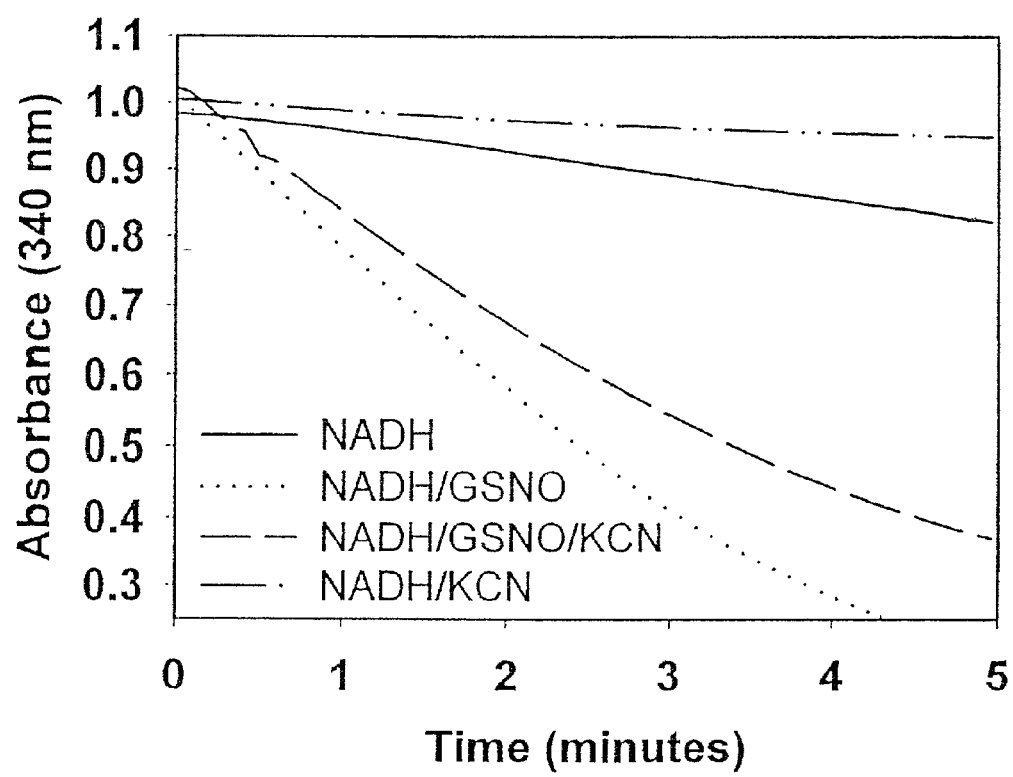

FIG. 10C is a graph showing measurements of the absorbance at 340 nm (peak absorbance of NADH) over time, in samples of 75 μg/ml purified HMP in buffer and 0.1 mM NADH, after the addition of 0.5 mM GSNO (dotted line), 1 mM cyanide (dash and dot line), both (dashed line), or neither GSNO nor cyanide (solid line). Starting absorbances were normalized to a value of 1.

Figure 10D:
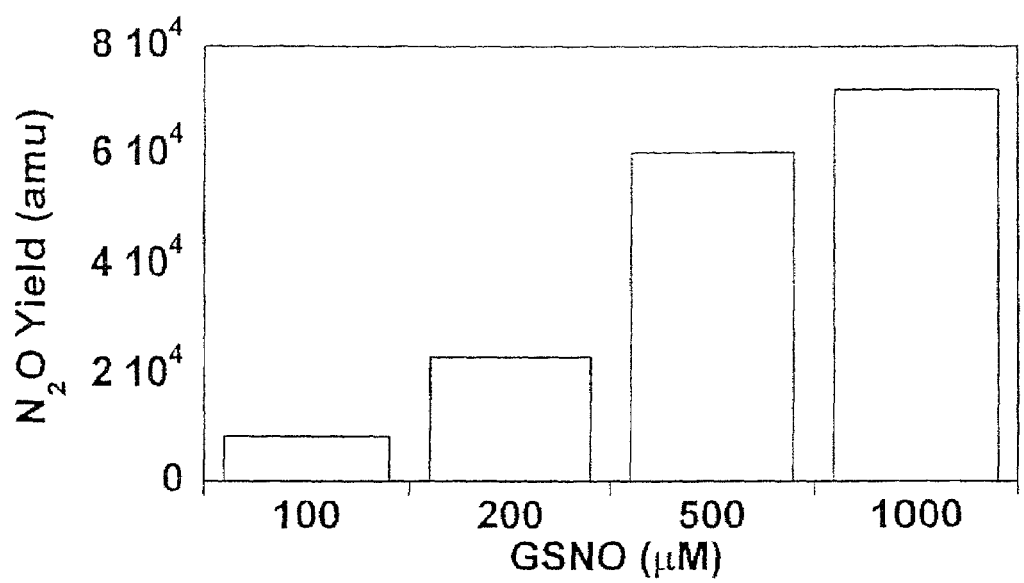

FIG. 10D is a bar graph illustrating $N_2O$ as the main product of aerobic GSNO reduction by purified HMP. The level of each bar indicates $N_2O$ production as monitored (Arnelle D. R. and Stamler, J. S., Arch. Biochem. Biophys. 318:279–285 (1995)) following 1 hour of incubation of the indicated concentrations of GSNO with 0.5 mM NADH and 75 μg/ml HMP. The yield shown is normalized to nitrogen (minus the yield produced in the absence of enzyme). Nitrite (2%) and nitrate (5%) were minor products.

Figure 11A:
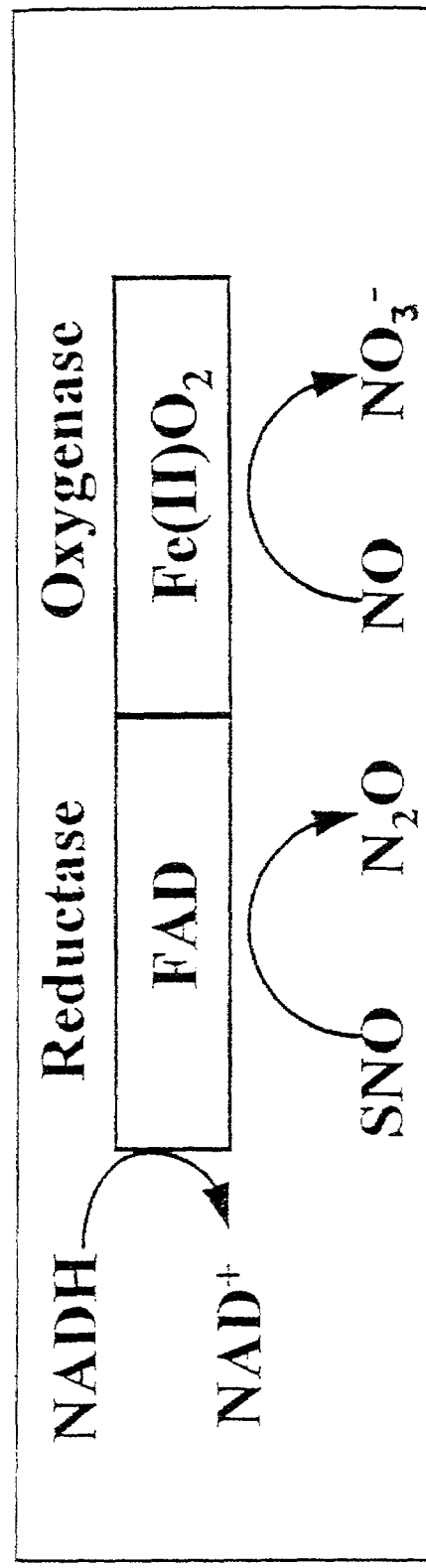

FIG. 11A is a diagram of a scheme showing the reductase and oxygenase activities of HMP. The schematic of the enzyme is derived from the structural basis of electron transfer (Ermler, U, et al, EMBO J., 14:6067–6077 (1995)).

Figure 11B:
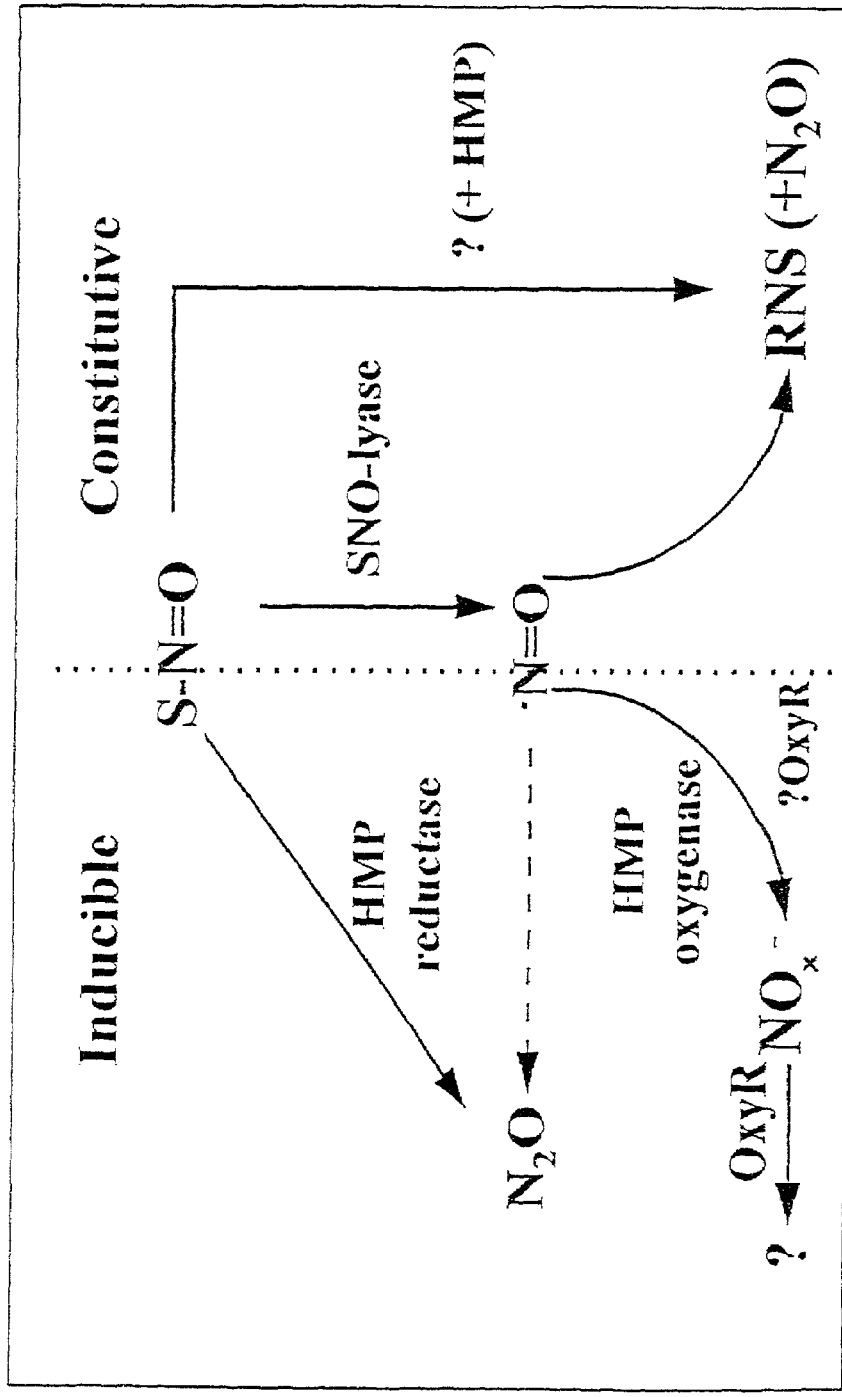

FIG. 11B is a diagram of a scheme showing metabolic pathways for S-nitrosothiol (SNO) and NO breakdown in bacteria. SNO is cleaved to NO by constitutive SNO-lyases or reduced by inducible HMP-reductase to $N_2O$. NO then partly autooxidizes to yield reactive nitrogen species (RNS) or is oxidized to $NO_x$ by the inducible HMP-oxygenase. The metabolic fate and/or production of $NO_x$ is determined by oxyR controlled genes (Hausladen, A. et al., Cell 86:719–729 (1996)). A small amount of SNO or NO may be converted by HMP-reductase to $N_2O$ in the constitutive metabolism-pathway and inducible anaerobic metabolism-pathway, respectively.

Figure 12A:
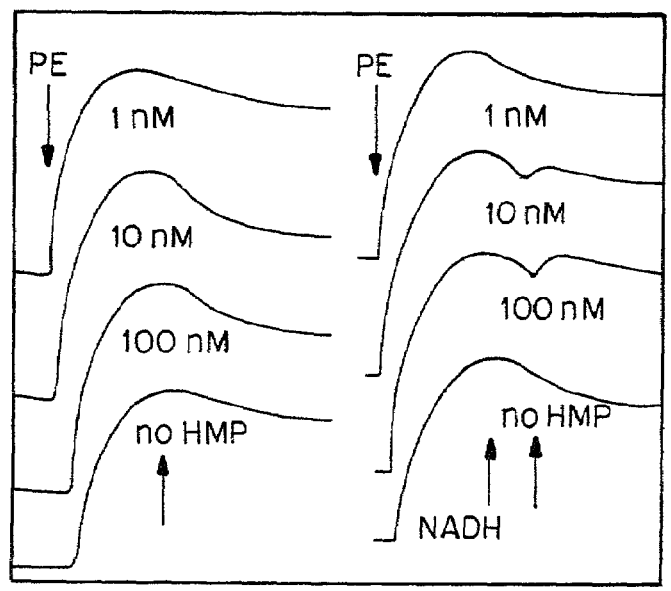

FIG. 12A is a reproduction of traces from force transducers measuring isometric tone in rabbit aortic ring segments. Rings were preconstricted with phenylephrine (PE). HMP was then added at the indicated concentrations in the absence (left 4 traces) or presence (right 4 traces) of 0.1 mM NADH.

Figure 12B:
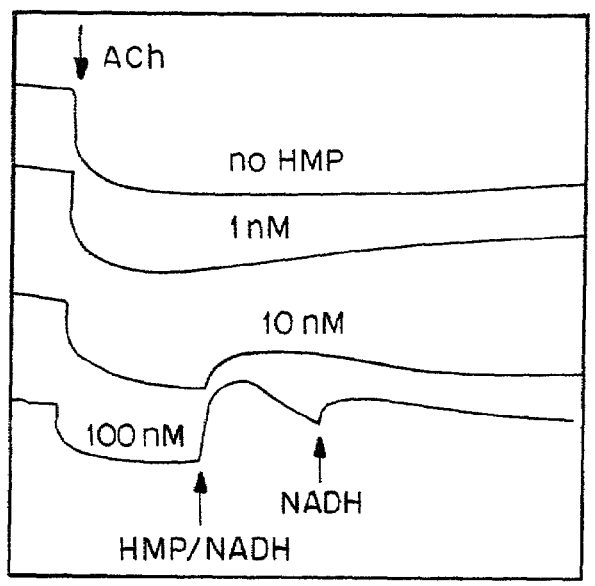

FIG. 12B is a reproduction of traces from force transducers measuring isometric tone in rabbit aortic ring segments. EDRF/NO dependent relaxation was induced by addition of acetycholine (ACh), 0.1 mM NADH and the indicated concentrations of HMP were then added. For the assay containing 100 nM HMP, a second dose of 0.1 mM NADH was made at the arrow.

Figure 13:
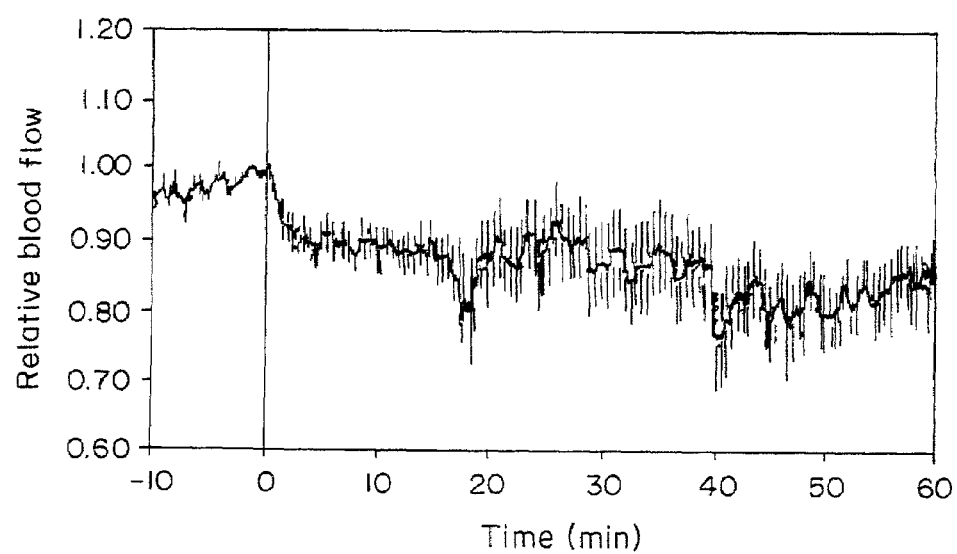

FIG. 13 is a plot of relative blood flow versus time. Blood flow was measured using laser Doppler in a dorsal flap window chamber preparation. Hemoglobin infusion (t=0 min) minimally reduces blood flow in a mammary adenocarcinoma model.

Figure 14:
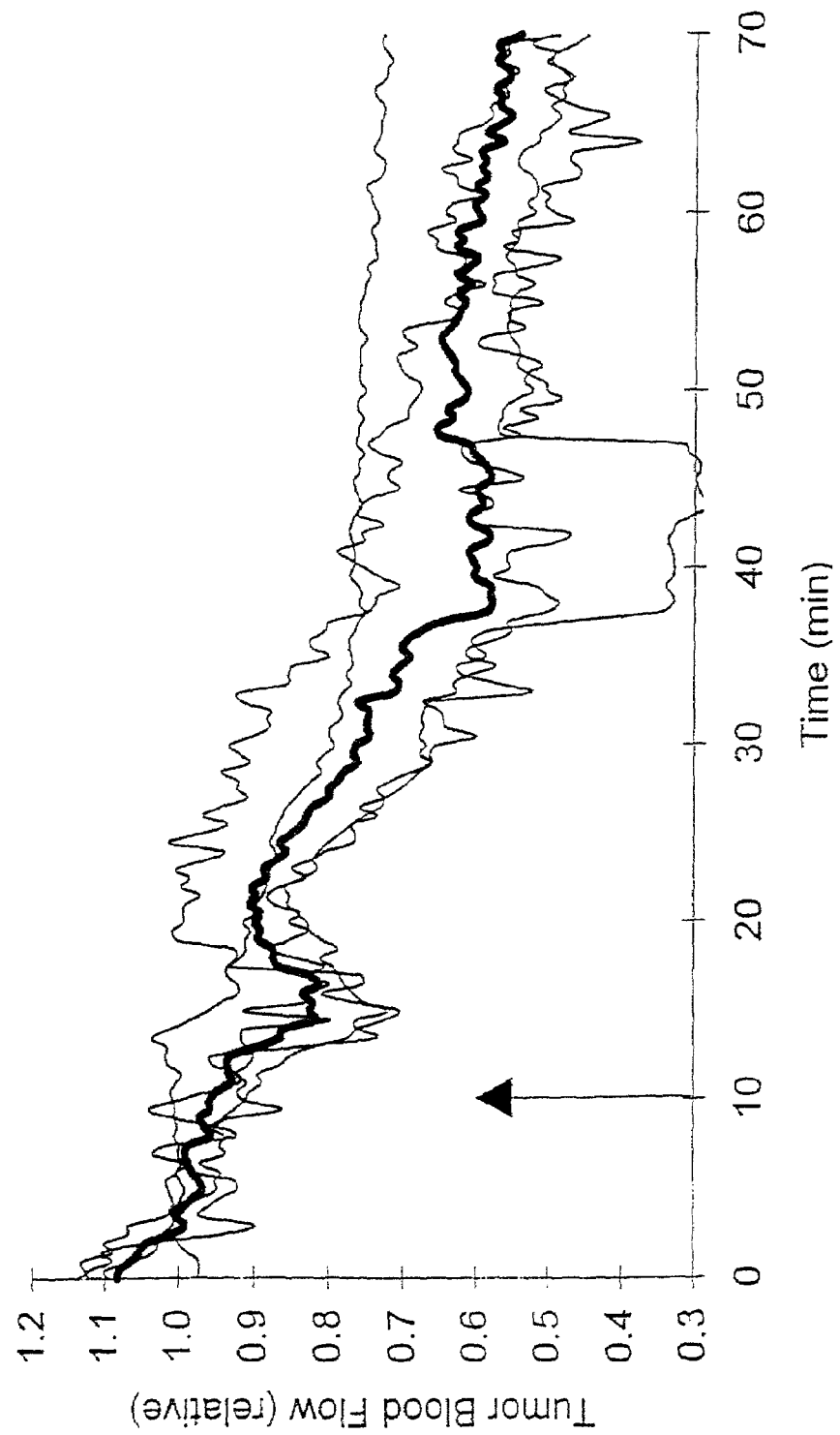

FIG. 14 is a graph of relative tumor blood flow versus time (minutes) showing a decrease in tumor blood flow induced by 25 mg/kg NO dioxygenase IV (HMP) in Fischer rats bearing a rat mammary adenocarcinoma (R3230Ac) in the hindlimb. Tumor blood flow was measured using a laser Doppler flow probe (Oxford, UK). Systemic hemodynamics do not change. Each curve represents one rat. The heavy black line is the mean. The vertical arrow at 10 minutes indicates the infusion of NO dioxygenase.

DETAILED DESCRIPTION OF THE INVENTION

The parasitic nematode *Ascaris lumbricoides* infects one billion people worldwide. Its perienteric fluid contains a hemoglobin that binds oxygen nearly 25,000 times more tightly than human hemoglobin. Despite numerous investigations over the past fifty years, the biological function of this molecule has remained elusive. The distal heme pocket contains a metal, oxygen, and thiol (Yang, J., et al, *Proc. Natl. Acad. Sci. USA* 92: 4224–4228 (1995)), all known to be reactive with nitric oxide (NO) or related molecules.

*Ascaris lumbricoides* contains abundant quantities of an extraordinarily oxygen-avid hemoglobin ($P_{50}$ 0.001–0.004 mm Hg) (Davenport, H. E., *Proc. R. Soc. London Ser. B*, 136:355–270 (1949); Okazaki, T. & Wittenberg, J. B., *Biochim. Biophys. Acata*, 111:503–511(1965)). *Ascaris* hemoglobin (AH) contains a total of 16 globin units; there are eight identical polypeptides each with two tandem globin folds (Darawshe, S., et al., *Biochem. J.*, 242:689–694 (1987); Sherman, D. R., et al., *Proc. Natl. Acad. Sci. USA*, 89:11696–11700 (1992)). The high oxygen avidity allows AH to remain fully liganded in the low oxygen tension of the gut. Tight oxygen binding is the result of a very slow rate of oxygen dissociation, whereas the on-rate for oxygen is similar to mammalian hemoglobins (Davenport, H. E., *Proc. R. Soc. London Ser. B*, 136:355–270 (1949); Okazaki, T. & Wittenberg, J. B., *Biochim. Biophys. Acta* 111:503–511 (1965)). Comparison to other invertebrate hemoglobins, mutagenesis, spectroscopic analysis, and elucidation of the crystal structure of the first globin domain (D1) of AH have unraveled the molecular basis for the high oxygen avidity. (Yang, J., et al., *Proc. Natl. Acad. Sci. USA*, 92:4224–4228 (1995); De Baere, I., et al., *Proc. Natl. Acad. Sci USA*, 91:1594–1597(1994); Huang, S., et al, *J. Biol. Chem.* 271: 958–963 (1996); Kloek, A. P., et al., *J. Biol. Chem.* 269: 2377–2379 (1994); Peterson, E. S., et al., *Biochem.* 36(42): 13110–13121 (1997)). That is, a strong hydrogen bond with the B10 tyrosine hydroxyl, as well as weak interaction with the distal E7 glutamine residue, stabilize liganded oxygen. As AH possesses such a high affinity for oxygen, it seems unlikely that its function is oxygen delivery.

Flavohemoglobin (HMP), as described herein, possesses a (flavo)reductase detoxification mechanism for SNO and a metal-detoxification mechanism for NO (FIG. 11A). The reductase domain reduces GSNO to $N_2O$ independently of $O_2$ while the heme-containing domain oxidizes NO to nitrate (and nitrite). Thus, $N_2O$ is the sole product of enzyme catalysis under anaerobic conditions, while $NO_x^-$ is also produced in the aerobic mechanism. The reactions of GSNO and NO with mammalian hemoglobins are quite different: they result in peroxynitrosyl, (Wade, R. S. and Castro, C. E., *Chem. Res. Toxicol.* 9:1382–1390 (1996); Eich, R. F. et al., *Biochemistry*, 35:6976–6983 (1996)), and thionitrosyl derivatives (Jia, L. et al., *Nature* 380:221–226 (1996)) which have pluripotent antimicrobial activities (MacMicking, J. D. et al., *Proc. Natl. Acad. Sci. USA* 94:5243–5248 (1997), DeGroote, M. A. et al., *Science* 272: 414–417 (1996), Hausladen, A. et al., *Cell* 86:719–729 (1996), DeGroote, M. A. et al., *Proc. Natl. Acad. Sci. USA.* 94:13997–14001 (1997). By thus marrying a reductase module to the globin domain Zhu, H. & Riggs, A. F. *Proc. Natl. Acad. Sci. USA*, 89:5015–5019 (1992); Andrews, S. C. et al., *FEBS Lett.* 302:247–252 (1992)), HMP has apparently evolved the means to protect bacteria from these harmful chemical reactions.

Studies described in the Exemplification herein reveal an emerging picture of novel metabolic pathways and tightly regulated detoxification mechanisms for both SNO and NO by HMP (FIG. 11B). A constitutive aerobic-metabolism pathway that gives rise to nitrite capitalizes on several lyases that convert GSNO to NO, and low levels of HMP which catalyze substrate transformation directly. Constitutive anaerobic-reduction of GSNO is much less efficient and highlights the importance of the lyase activities. Components of these pathways may be involved in either stress-responses or homeostatic mechanisms, including well-known NO functions. The bacterial cell also contains NO and SNO-responsive genes which are induced when reactive nitrogen species exceed a dangerous threshold (Hausladen, A. et al., *Cell* 86:719–729 (1996)). Flavohemoglobin plays a central role in the inducible metabolic pathways adapted for detoxification. In the aerobic mechanism of HMP, GSNO is directly metabolized to $N_2O$, and NO that escapes or it otherwise generated, is oxidized enzymatically to $NO_x^-$. OxyR then determines the metabolic fate of nitrite; (Hausladen, A. et al., *Cell* 86:719–729 (1996)), (or otherwise influences its accumulation) by exerting control over genes that may be involved in both reductive and oxidative mechanisms. In the anaerobic pathway, HMP reduces GSNO (and perhaps NO) to $N_2O$. A SNO deficiency has recently been identified in asthma (Gaston, B. et al., *Lancet* 351(9112): 1317–1319, 1998). This raises the possibility that defects in (S)NO metabolism pathways may contribute to human disease.

As described herein, a study of *Ascaris* hemoglobin (AH) was conducted. In the course of the study it was determined that *Ascaris* hemoglobin can enzymatically consume oxygen in a reaction which is accelerated by NO. Mechanistically, this oxygen consuming reaction involves unprecedented chemistry of a heme, thiol, NO redox triplet. In further studies, it was determined that myoglobin (Example 3) and flavohemoglobin can also catalyze the consumption of oxygen. This demonstration of deoxygenase activity by representative members of three entirely distinct classes of hemoproteins (i.e., *Ascaris* hemoglobin, myoglobins and flavohemoglobins) indicates that deoxygenase activity is a general characteristic of hemoproteins.

These results indicate the presence of additional reaction pathways for oxygen, beyond fixation as nitrate, which are primed by NO. A peroxidase or oxidase reaction is a reasonable possibility since hemoglobins are known to carry out peroxidase/oxidase functions that may be catalyzed by NO-related species (Landino, L. M., et al., *Proc. Natl. Acad. Sci. USA*, 93:15069–15074 (1996); Lissi, E., *Free Radical Biol. & Med.*, 24(9):1535–1536 (1998); Maccarrone, M., et al., *FEBS Lett.*, 410:470–476 (1997)). Additional redox cofactors, such as the E19 thiol within AH, are known to support this chemistry in hemoglobins (Balagopalakrishna, C., et al., *Biochem.*, 37:13194–13202 (1998) (equations (1) and (2)). Alternatively, oxygen consumption may be attributed to the P450-like activity of hemoglobin.

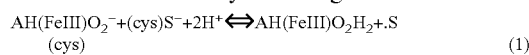

$$AH(FeIII)O_2^- + (cys)S^- + 2H^+ \Leftrightarrow AH(FeIII)O_2H_2 + S(cys) \quad (1)$$

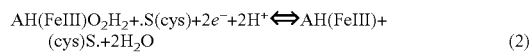

$$AH(FeIII)O_2H_2 + S(cys) + 2e^- + 2H^+ \Leftrightarrow AH(FeIII) + (cys)S + 2H_2O \quad (2)$$

From the data described herein, a model for the consumption of $O_2$ and NO by AH was constructed, which is presented herein as an illustration and is not intended to be limiting. The distal pocket of AH contains a strong hydrogen bonding network between liganded oxygen, B10 tyrosine, and E7 glutamine, (Yang, J., et al., *Proc. Natl. Acad. Sci.*

USA, 92:4224–4228 (1995); Peterson, E. S., et al, *Biochem.*, 36(42):13110–13121 (1997)). The liganded oxygen has a strong superoxide character (Example 1, equation (5)), which requires hydrogen bonding for stability, as evidenced by the rapid rate of autooxidation of mutants with B10 tyrosine changed to phenylalanine or leucine (De Baere, I., et al., *Proc. Natl. Acad. Sci USA,* 91:1594–1597(1994); Kloek, A. P., et al., *J. Biol. Chem.,* 269:2377–2379 (1994)). Examination of the autooxidation of human hemoglobin has led to the proposal that oxidation occurs via a proton relay involving the distal histidine residue (Balagopalakrishna, C., et al., *Biochem.,* 35:6393–6398 (1996)). In AH, the distal glutamine and tyrosine have high $pK_a$'s, thus protonation will not occur at physiologic pH. AH-bound superoxide is, therefore, stable under most conditions. However, NO is highly diffusible and able to enter the distal pocket, producing heme oxidation and nitrate (Example 1, equation (6)).

Once methemoglobin of *Ascaris* is generated, it efficiently binds NO (Example 1, equation (7)); the presence of a distal glutamine speeds the reaction. Photolysis chemiluminescence and stopped-flow analyses suggest that the AH(FeIII) NO intermediate is in equilibrium with SNO(E15cys) (Example 1, equation (8)). This conclusion is also supported by the ability of S-nitrosocysteine to oxidize hemes in native AH but not in mutants deficient in E15 cysteine. Oxygen will then bind to the ferrous heme of SNO-containing molecules (Example 1, equation (9)), which can generate an unstable peroxynitrosyl complex within the distal pocket, which decomposes to produce nitrate (Example 1, equations (10)–(13)). Involvement of (thiyl) radical chemistry (equation (10)) is consistent with a peroxidase function (Landino, L. M., et al., *Proc. Natl. Acad. Sci. USA,* 93:15069–15074 (1996); Lissi, E., *Free Radical Biol. & Med.,* 24(9):1535–1536 (1998); Maccarrone, M., et al., *FEBS Lett.,* 410:470–476 (1997)), but alternative schemes can be invoked. Moreover, Balagopalakrishna et al. have recently shown thiyl radical-induced peroxide (FeIII) heme complex) generation in mammalian hemoglobin (Balagopalakrishna, C., et al., *Biochem.,* 3 7:13194–13202 (1998)). It is not clear which NO-related species primes AH for $O_2$ metabolism; however, the peroxynitrosol intermediate is an excellent catalytic candidate. By serving as substrate for such hemoproteins, peroxynitrite is known to activate peroxidase activity (Landino, L. M., et al., *Proc. Natl. Acad. Sci. USA,* 93:15069–15074 (1996)). These mechanistic issues notwithstanding, the data described herein clearly demonstrate that *Ascaris* hemoglobin consumes NO and oxygen in a NADPH-dependent manner. *Ascaris suum* adults metabolize anaerobically (Komuniecki, P. R., et al., *Exp. Parasitol.,* 76:424–437 (1993)), and it is thought that free oxygen is highly toxic (Blaxter, M. L., *Parasitol. Today,* 9:353–360 (1993)). Thus, *Ascaris* hemoglobin is a nitric oxide-activated deoxygenase, that can utilize endogenously produced NO as a cosubstrate to detoxify oxygen (Example 2).

In the phylogeny of hemoglobins, nematode sits at the divide, between the primordial bacterial flavohemoglobins, which have been recently discovered to function in NO detoxification (Crawford, M. J and Goldberg, D. E., *J. Biol. Chem.,* 273:12543–12547 (1998); Hausladen, A., et al., *Proc. Natl. Acad. Sci. USA,* 95:14100–14105 (1998)), and the cooperative mammalian hemoglobins, which have been recently discovered to function in NO delivery (Gow, A. J. & Stamler, J. S., *Nature,* 391:169–173 (1998); Jia, L., et al., *Nature,* 380: 221–226 (1996); Stamler, et al., *Science,* 276: 2034–2037 (1997)). A NAD(P)H dependent reductase activity supports NO metabolism in bacteria, whereas critical thiols subserve the NO donor function that regulates $O_2$ delivery in mammals. *Ascaris* hemoglobin appears to represent an "evolutionary bridge;" it retains a primitive enzymatic reductase function, but one designed to control oxygen tension analogous to the respiratory function of mammalian hemoglobins. Moreover, it controls this effect by utilizing NO, again analogous to mammalian hemoglobins, which have incorporated thiols into the heme pocket in order to preserve NO bioactivity (Gow, A. J. & Stamler, J. S., *Nature* 391:169–173 (1998); Jia, L., et al., *Nature* 380: 221–226 (1996); Stamler, et al., *Science* 276:2034–2037 (1997)). The positioning of a thiol in the distal pocket of AH as opposed to the proximal pocket of mammalian hemoglobin enables the alternative NO-related functions of deoxygenation and oxygenation, respectively. In other words, hemoglobins have transformed a primordial NO metabolism function into a respiratory function by incorporating thiols that enable the use of NO (FIG. 4). Although the primary function of AH appears to be oxygen removal in the nematode, it may also detoxify high amounts of NO generated by innate host defenses, reminiscent of bacterial flavohemoglobins that metabolize NO to nitrate (Hausladen, A., et al., *Proc. Natl. Acad. Sci. USA,* 95:14100–14105 (1998)).

The study of *Ascaris* hemoglobin described herein has uncovered novel NO chemistry involving enzymatic activity of a heme, thiol, NO redox triad. Furthermore, the previously unknown function of *Ascaris* hemoglobin, namely the detoxification of oxygen, has been delineated. The identification of a unique structural adaptation of *Ascaris* hemoglobin, which occurred 1500 million years ago, establishes a new paradigm in which hemoglobins have evolved for distinct NO-related functions.

The invention relates to hemoproteins and to the deoxygenase activity of hemoproteins. In one aspect, the invention relates to the hemoglobin of nematodes of the genus *Ascaris*, and a method of treating a mammal infected with *Ascaris* sp.

Free oxygen is toxic to *Ascaris* sp., and as described herein, AH functions as a NO-activated deoxygenase to detoxify oxygen. Thus, the administration of an agent which inhibits (reduces or prevents) the production of NO, such as a suitable NO synthase inhibitor, can result in inhibition of the deoxygenase activity of AH. Consequently, the concentration of free oxygen can rise to levels which are toxic to *Ascaris*.

In one aspect, the invention is a method of treating a mammal infected with a microbe or parasite which uses hemoglobin to regulate oxygen tension. In one embodiment, the invention is a method of treating a mammal infected with a nematode of the genus *Ascaris*. The method comprises administering an effective amount of an inhibitor of NO synthase to the infected mammal. The mammal can be infected with any species of the genus *Ascaris*, such as *Ascaris lumbricoides* or *Ascaris suum*.

Inhibitors of NO synthase which are suitable for use in the method of the invention can inhibit an *Ascaris* NO synthase, a mammalian NO synthase (e.g., endothelial cell NO synthase, inducible NO synthase, neuronal NO synthase) or a combination thereof. Several compounds which can inhibit NO synthase are known in the art, such as, L-arginine uptake inhibitors (e.g., L-lysine, L-ornithine, canavanine, homoarginine), arginase, NG-nitro-L-arginine, L-nitroarginine methyl ester, N-monomethyl-L-arginine, 2-ethyl-2-thiopseudourea, L-N6-(1-iminoethyl)lysine, aminoguanidine, 7-nitroindazole and the like. Additional compounds which can inhibit an NO synthase can be identified using suitable methods, such as the methods described in U.S. Pat. Nos. 5,883,251 and 5,874,472, the entire teachings of which are incorporated herein by reference. Inhibitors of NO synthase can be identified, for example, by screening libraries or collections of molecules, such as the Chemical Repository of the National Cancer Institute. Inhibitors identified in this manner can be used to treat a mammal infected with *Ascaris* sp.

Another source of compounds which can inhibit NO synthase are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods.

The particular NO synthase inhibitor chosen to treat the infected mammal will depend on a variety of factors, including the infecting species and the age, sex, weight, tolerance to drugs and general health of the mammal. The skilled practitioner will be able to choose the most appropriate NO synthase inhibitor to administer based upon these and other considerations. In one example, a 50 year old male infected with *Ascaris* sp. and complaining of gastrointestinal upset can be treated with L-monomethylarginine at a dose of 0.1 mg/kg per day for three weeks.

According to the methods of the invention, one or more inhibitors of NO synthase can be administered to the mammal alone or with other therapeutic agents, such as anti-nematode agents (e.g., mebendazol, ivermectin), by an appropriate route. A therapeutically effective amount is administered. A therapeutically effective amount is an amount sufficient to achieve the desired therapeutic or prophylactic effect, under the conditions of administration, such as an amount which is sufficient to decrease the viability of *Ascaris* or to inhibit the activity of NO synthase. The NO synthase inhibitor and any other agent (e.g., anti-nematode agent) can be administered in a single dose or multiple doses. The dosage can be determined by methods known in the art and is dependent, for example, upon the particular hemoprotein and other agent chosen, the mammal's age, sensitivity and tolerance to drugs, and overall well-being.

A variety of routes of administration are possible including, for example, oral, dietary, topical, transdermal, rectal, parenteral (e.g., intravenous, intraarterial, intraperitoneal, intramuscular, intrathecal, intracerebral, subcutaneous injection, intradermal injection), and inhalation (e.g., intrabronchial, intranasal or oral inhalation, intranasal drops) routes of administration, depending on the NO synthase inhibitor and disease or condition to be treated. Administration can be local or systemic as indicated. The preferred mode of administration can vary depending upon the particular NO synthase inhibitor chosen; however, oral or parenteral administration is generally preferred.

The NO synthase inhibitor can be administered to the mammal as part of a composition comprising an NO synthase inhibitor and a pharmaceutically or physiologically acceptable carrier. Formulation will vary according to the route of administration selected (e.g., solution, emulsion, capsule). Suitable physiological carriers can contain inert ingredients which do not interact with the NO synthase inhibitor. Standard pharmaceutical formulation techniques can be employed, such as those described in Remington's Pharmaceutical Sciences, Mack Publishing Company, Easton, Pa. Suitable physiological carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents," John Wiley and Sons, 1986). For inhalation, the agent can be solubilized and loaded into a suitable dispenser for administration (e.g., an atomizer, nebulizer or pressurized aerosol dispenser).

In another aspect, the invention relates to therapeutic methods wherein a hemoprotein (e.g., globin, cytochrome) with deoxygenase activity and NO-consuming activity is administered to a mammal.

All hemoproteins are capable of redox chemistry to some extent, however, while cytochromes are well known oxidases/reductases, globins (e.g., hemoglobins, myoglobins) have been thought to function principally in oxygen delivery. Generally, any redox reactions which can be detected in reaction systems containing globins have been regarded as trivial side reactions. As described herein, globins can function as enzymes which catalyze redox reactions (e.g., NO-activated deoxygenation), when appropriate substrates and/or cofactors (e.g., NO, NADH, NADPH) are present in suitable concentrations. In fact, the dominant function of certain of the globins is redox chemistry. For example, flavohemoglobin-catalyzed deoxygenation can protect bacteria from the toxic effects of NO, and AH-catalyzed deoxygenation can protect *Ascaris* from toxic levels of $O_2$, as described herein. Furthermore, studies have shown that myoglobin is not required to meet the metabolic requirements of exercise or pregnancy in mice (Garry D. J., *Nature* 395:905–908 (1998)), indicating that the primary function of myoglobin may be the regulation of oxygen tension.

As used herein, the term "NO-activated deoygenase activity" refers to an enzymatic activity (i.e., a catalytic activity) that promotes a chemical reaction which consumes oxygen ($O_2$), given a reducing agent, wherein the catalytic rate (e.g., the rate of oxygen consumption) is accelerated when NO is present in the reaction system. For example, in the absence of NO, the oxygen consuming reaction promoted by a protein having NO-activated deoxygenase activity can proceed slowly, so that the consumption of a reactant (e.g., oxygen, NO) and/or the accumulation of a product is relatively low. However, when NO is introduced into the reaction system, a higher rate of reactant (e.g., oxygen, NO) consumption and/or product accumulation can be measured using suitable methods, such as the methods described herein.

The hemoprotein can be a naturally occurring protein which has deoxygenase activity (which can be NO-activated), an active variant thereof or an enzymatically active fragment of a naturally occurring enzyme or active variant thereof. A variant hemoprotein typically differs in amino acid sequence from another reference hemoprotein. Generally, differences are limited so that the sequences of the reference polypeptide and the variant are closely similar overall and, in many regions, identical. A variant hemoprotein and a reference hemoprotein can differ in amino acid sequence by one or more amino acid substitutions, additions, deletions, truncations, fusions or any combination thereof. Variant hemoproteins include naturally occurring variants (e.g., allelic forms) and variants which are not known to occur naturally. Non-naturally occurring variant hemoproteins can be produced using suitable methods, for example, by direct synthesis, mutagenesis (e.g., site directed mutagenesis, scanning mutagenesis) and other methods of recombinant DNA technology. Hemoproteins and variants thereof which have deoxygenase activity can be identified using suitable assays, such as the oxygen consumption and NO metabolism assays described herein. Preferably, the hemoprotein is a globin or active variant thereof. More preferably the hemoprotein is AH, a myoglobin (e.g., human, horse), a flavohemoglobin (e.g., *Escherichia coli, Salmonella* sp., *Mycobacterium tuberculosis*) or an active variant of any of the foregoing.

The hemoprotein to be administered can be produced using suitable methods. For example, the hemoprotein can be obtained from cells in which it is produced (e.g., bacteria, yeast, reticulocytes, recombinant cells) using conventional methods (e.g., homogenization, precipitation, differential centrifugation, chromatography, preparative electrophoresis). In one embodiment, the hemoprotein is isolated from the cells in which it is produced in nature. The term "isolated" as used herein indicates that the hemoprotein exists in a physical milieu which is distinct from that in which it occurs in nature. For example, the isolated hemoprotein can be substantially isolated with respect to the complex cellular milieu in which it naturally occurs, and can be purified essentially to homogeneity, for example as determined by analytical electrophoresis or chromatography (e.g., HPLC).

In one embodiment, the invention is a method of enzymatically reducing the concentration of oxygen, nitric oxide or a combination thereof, in a mammal. The method comprises administering a therapeutically effective amount of a hemoprotein having deoxygenase activity to a mammal in need of such therapy. A hemoprotein can be administered individually or in combination with one or more other hemoproteins or with other therapeutic agents or methods of therapy.

In another embodiment, the invention is a method of treating a mammal with a disorder characterized by pathologically proliferating cells. The method comprises administering a therapeutically effective amount of a hemoprotein having NO-activated deoxygenase activity to a mammal in need of such therapy. As used herein, the phrase "pathologically proliferating cell" refers to cells which contribute to a pathological state as a result of proliferation. A "pathologically proliferating cell" can be cancerous or non-cancerous and can contribute to the pathology of, for example, tumors, prostatic hypertropy, psoriasis and restenosis.

In additional embodiments, the invention relates to a method of treating (reducing the size of or slowing or preventing growth of) tumors, such as those occurring in the disorder commonly referred to as cancer (e.g., sarcoma, carcinoma, adenoma, lymphoma, leukemia). In one embodiment, the invention is a method of deoxygenating a tumor, comprising administering a therapeutically effective amount of a hemoprotein having NO-activated deoxygenase activity to a mammal having a tumor. The term "deoxygenate" as used herein refers to an enzyme catalyzed reduction in oxygen tension to produce an area of hypoxia. The deoxygenation of tumors can result in decreased proliferation of tumor cells and can enhance the efficacy of, or sensitize cells to, certain therapies. For example, deoxygenation of tumors can increase the efficacy of certain cytotoxic agents, such as, the class of hypoxia activated cytotoxins which are generally referred to as bioreductive cytotoxic agents. The hemoprotein having NO-activated deoxygenase activity can be administered to the mammal before, after or concurrently with a bioreductive cytotoxic agent or other therapy.

Generally, bioreductive cytotoxic agents, such as nitroaromatic compounds (e.g., 2-nitroimidazoles (e.g., misonidazole, etanidazole), 1,2,4-benzotriazine dioxides (e.g., tyrapazamine), quinones (e.g., mitomycin C), are administered as inactive prodrugs which become cytotoxic when metabolized under hypoxic conditions. Consequently, these agents can be used to preferentially kill cells in areas of hypoxia. Thus, in another embodiment, the invention is a method of potentiating the cytotoxic activity of a cytotoxic agent (e.g., a bioreductive agent), comprising administering a therapeutically effective amount of one or more hemoprotein(s) having NO-activated deoxygenase activity and a therapeutically effective amount of one or more cytotoxic agent(s) to a mammal with one or more tumor(s). In still another embodiment, the invention is a method of antitumor therapy, comprising administering a therapeutically effective amount of a hemoprotein having NO-activated deoxygenase activity and a therapeutically effective amount of a cytotoxic agent (e.g., a bioreductive agent) to a mammal with a tumor. See, for example, Kelson, A. B. et al., *Anticancer Drug Design* 13:575–592 (1998); Rauth, A. M. et al., *Int. J. Radiation Oncology Biol. Phys.* 42:755–762 (1998), regarding bioreductive agents. In one example of the invention, a man having a tumor, which did not regress upon treatment with a standard regimen of chemotherapy, can be treated with a standard dose of a chemotherapeutic agent in conjunction with a hemoprotein having NO-activated deoxygenase activity at a dose of 1 mg/kg which is infused over one hour.

The catalytic reactions described herein (equations 1, 2, 5–13, and equations 14–17) and in Hausladen, A., et al., *Proc. Natl. Acad. Sci. USA,* 95:14100–14105 (1998), comprise the generation of reactive oxygen species (e.g., superoxide, hydrogen peroxide) as intermediates. Under certain conditions, such reactive oxygen species can accumulate. For example, when little or no nitric oxide and a large amount of a reducing agent (e.g., about 5 mM or more) are present, superoxide and/or hydrogen peroxide can be preferentially produced by AH, myoglobins and flavohemoglobins. An illustration of a possible mechanism at the heme iron by which flavohemoglobins can produce reactive oxygen species is presented as equations (3), (3a), (3b) and (4).

$$Fe(III) + NADH \rightarrow Fe(II) + NAD^+ \tag{3}$$

$$Fe(II) + O_2 \rightarrow Fe(II)O_2 \tag{3a}$$

$$Fe(II)O_2 \rightarrow Fe(III)O_2^- \tag{3b}$$

$$Fe(II)O_2 \rightarrow Fe(III) + O_2^- \tag{4}$$

As shown in Example 3, equations (14)–(17), the chemistry of $O_2$ consumption by myoglobin is relatively complex. A mechanism by which myoglobins can produce reactive oxygen species comprises a reaction between the superoxide intermediate produced in equation (14) and $MbFe(II)O_2$ to produce hydrogen peroxide, $O_2$ and $MbFe(III)$. The $MbFe(III)$ produced can be reduced by NADH, and then bind $O_2$ and react with another superoxide anion. NO can differentially affect the generation of reactive oxygen species by myoglobin, depending on the reaction conditions. For example, NO accelerates the reaction when a low concentration (e.g., about 100 μM or less) of reducing agent is used, and NO inhibits the reaction when a high concentration (e.g., about 5 mM or more) of reducing agent is used.

In another embodiment, the invention is a method of enzymatically generating toxic reactive oxygen species (e.g., hydrogen peroxide, superoxide) for therapeutic purposes, e.g., to treat a disorder characterized by pathologically proliferating cells. The method comprises administering an effective amount of a hemoprotein (e.g., a hemoprotein having NO-activated deoxygenase activity) to a mammal in need of such therapy. In one embodiment, the method further comprises the administration of a reducing agent. In one example, a flavohemoglobin and NADH are administered locally to produce an area enriched in toxic reactive oxygen species by virtue of their production. In another example, AH is administered systemically and NADH is administered locally by injection into a tumor. In this example, the tumor can become enriched in toxic reactive oxygen species by virtue of their production. Additional therapeutic agents or processes can be targeted to the area enriched in reactive oxygen species, resulting in superior therapy. For example, cytotoxic agents with a mechanism of action that comprises the generation of reactive oxygen species such as anthracyclin-derivatives (e.g., adriamycin) can be administered. If desired, cytotoxic agents or other therapeutic agents can be targeted to tumors by encapsulating them in liposomes, optionally with a reducing agent such as NADPH. In addition, the area enriched in reactive oxygen species by the enzymatic reaction can be irradiated.

In another aspect, the invention is a composition comprising a hemoprotein having deoxygenase activity (e.g., AH, a myoglobin, a flavohemoglobin) or an active fragment thereof and a physiologically acceptable carrier. The composition can further comprise a cytotoxic agent (e.g., an anti-tumor agent), a reducing agent (e.g., a biological reducing agent) and/or a NO donor as a source of NO, as described herein. In a preferred embodiment, the cytotoxic agent is a bioreductive cytotoxic agent.

According to the methods of the invention, one or more hemoproteins and/or other therapeutic agents (e.g., NO synthase inhibitor, cytotoxic agent) can be administered to the mammal by an appropriate route. A therapeutically effective amount of a hemoprotein and/or other agent is administered. A therapeutically effective amount is an amount sufficient to achieve the desired therapeutic or prophylactic effect, under the conditions of administration, such as an amount which is sufficient to reduce the concentration of oxygen (e.g., deoxygenation), reduce the concentration of nitric oxide, inhibit the activity of NO synthase, potentiate the cytotoxic activity of a cytotoxic agent, produce an area enriched in toxic reactive oxygen species, decrease the rate of proliferation of tumor cells or kill tumor cells. The hemoprotein and any other agent (e.g., cytotoxic drug) to be administered can be administered in a single dose or multiple doses. The dosage can be determined by methods known in the art and is dependent, for example, upon the particular hemoprotein and other agent chosen, the type of disorder (e.g., type of tumor), the mammal's age, sensitivity and tolerance to drugs, and overall well-being.

As described herein, the deoxygenase activity of hemoproteins can be enhanced by reducing agents, such as biological reducing agents (e.g., NADH, NADPH, biopterin, flavins, and thiols such as N-acetylcysteine or other reducing agents present in cells). Thus, a reducing agent can be administered together with a hemoprotein or with a hemoprotein and another agent in accordance with the therapeutic methods of the invention. In one example, N-acetylcysteine (100 mg/kg) is administered together with AH (1 mg/kg).

A variety of routes of administration are possible including, for example, oral, dietary, topical, transdermal, rectal, parenteral (e.g., intravenous, intraarterial, intraperitoneal, intramuscular, intrathecal, intracerebral, subcutaneous injection, intradermal injection), and inhalation (e.g., intrabronchial, intranasal or oral inhalation, intranasal drops) routes of administration, depending on the hemoprotein and/or agent and disease or condition to be treated. Administration can be local or systemic as indicated. The preferred mode of administration can vary depending upon the particular hemoprotein and/or agent chosen, and the particular condition (e.g., disease) being treated, however, parenteral administration is generally preferred.

The hemoprotein and any additional therapeutic agents can be administered as a neutral compound or as a physiologically acceptable salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The hemoprotein and/or agent can be administered to the mammal as part of a composition comprising an isolated hemoprotein and a pharmaceutically or physiologically acceptable carrier. Formulation will vary according to the route of administration selected (e.g., solution, emulsion, capsule). Suitable physiological carriers can contain inert ingredients which do not interact with the hemoprotein and/or agent. Standard pharmaceutical formulation techniques can be employed, such as those described in Remington's Pharmaceutical Sciences, Mack Publishing Company, Easton, Pa. Suitable physiological carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents," John Wiley and Sons, 1986). For inhalation, the agent can be solubilized and loaded into a suitable dispenser for administration (e.g., an atomizer, nebulizer or pressurized aerosol dispenser). In addition, the hemoprotein can be complexed into liposomes or micelles, optionally with reducing agent and/or cytotoxic agent, as a method of preferentially targeting tumor cells. Flavohemoglobin, for example, can be administered in combination with other drugs, or can be administered in combination with sources of flavin, such as NADH and/or with biologically compatible thiols, such as glutathione.

Furthermore, the hemoprotein can be administered via in vivo expression of the recombinant protein. In vivo expression can be accomplished via somatic cell expression according to suitable methods (see, e.g. U.S. Pat. No. 5,399,346). In this embodiment, a nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The hemoproteins having deoxygenase activity can be used to reduce the concentration of oxygen in an aqueous solution with a pH of about 3 to about 8. Preferably, for deoxygenases having NO-activated deoxygenase activity, the aqueous solution comprises NO, or NO is added to the solution either directly (e.g., by bubbling NO through the solution) or indirectly. NO can be added to a solution indirectly by adding one or more NO synthase enzymes and suitable substrates (e.g., arginine), or a suitable NO donor (e.g., DEANO) to the solution. A variety of suitable NO donors are known in the art (see, for example, Feelisch, M. and Stamler, J. S. "Donors of Nitrogen Oxides" in: Eds., Feelisch, M. and Stamler, J. S., *Methods in Nitric Oxide Research*, John Wiley and Sons, Chichester, UK, pp. 71–115 (1996)). The aqueous solution can comprise a variety of solutes (e.g., organic ions, inorganic ions, detergents) and/or organic solvents. The quantity of solutes and/or organic solvent in the aqueous solution can affect the rate of deoxygenation. The maximum concentration of particular solutes and/or organic solvents which permit deoxygenation to proceed at the desired rate can be readily determined using conventional methods. Thus, hemoproteins having NO-activated deoxygenase activity find use in industrial applications where it is desirable to reduce the concentration of oxygen.

As used herein, "NO" and "nitric oxide" include the biologically active forms of nitric oxide identified as being responsible for physiological functions such as smooth muscle cell relaxation, killing of bacteria and killing of bacteria by white blood cells, synaptic transmitter function, release of adrenaline from adrenal medulla, gut peristalsis, regulation of penile tone and inhibition of blood clotting. "NO" includes the free radical form as well as nitroxyl anion ($NO^-$) and nitrosonium ($NO^+$). Nitrosothiols (SNO), formed by nitrosylation of thiols, can act as "carriers" of NO, in effect, extending the short physiological half-life of NO. Thus, carriers of NO can also be biologically active forms of nitric oxide.

In another aspect, the invention relates to a method for engineering an oxygen lowering enzyme. In one embodiment, a hemoprotein having NO-activated deoxygenase activity can be mutated to produce a variant protein with enhanced deoxygenase activity. Preferably, the engineered variant metabolizes $O_2$ at a rate that is at least about twice that of the un-mutated enzyme. Such variant proteins can be prepared using a variety of suitable methods such as, site directed mutagenesis and/or random mutagenesis (e.g., in vitro or directed evolution (Wan et al., *Proc. Natl. Acad. Sci. USA* 95:12825–12831 (1998)). In another embodiment, a hemoprotein which does not have NO-activated deoxygenase activity can be mutated to produce a variant having deoxygenase activity. In one example, the three dimensional structure of a first hemoprotein which does not have NO-activated deoxygenase activity, or a subunit thereof, can be determined and compared to the structure of AH, or other suitable hemoprotein which has deoxygenase activity. Particular amino acid residues of the first hemoprotein can be mutated to produce a protein having a three dimensional structure which is similar to that of AH or another hemoprotein having deoxygenase activity. In anther example, a reductase domain (e.g., a cytochrome P450 reductase domain) can be added to a hemoglobin. In a further example, a cysteine residue can be introduced into a globin (e.g., myoglobin) to provide a thiol in close proximity to the ligand binding site, analogous to the E15 thiol of AH. The engineered variant enzymes can be evaluated using suitable catalytic assays, such as the assays described herein, and/or by structural determination.

HMP as a Therapeutic Agent

The flavohemoglobins (HMP) can be used for therapeutic purposes. It is demonstrated herein that HMP enzymatic activity constricts blood vessels by scavenging endogenous NO, but in contrast to hemoglobin of mammals, HMP only works in the presence of substrate NAD(P)H and operates at very low concentrations of HMP. As demonstrated in the Exemplification, using infusion of HMP into an animal tumor model, HMP changes blood flow to a tumor without altering systemic hemodynamics (i.e., blood pressure and heart rate).

Nitric oxide production has been implicated in a wide variety of pathological conditions. Excess NO biosynthesis by immune cells in sepsis causes potentially lethal hypotension. This pathophysiological manifestation of nitrosative stress has led to the search for effective NO scavengers that can be administered to constrict blood vessels. Hemoglobin, (Hb) which naturally subserves this function in mammals, has been extensively studied as a scavenger in septic shock. However, oxyHb is consumed (i.e., oxidized to metHb) in the reaction with NO, and cannot be easily reduced. To be effective, oxyHb is used at relatively high concentrations, increasing the potential for negative effects that may be associated with the administration of cell-free hemoglobin.

On the other hand, flavohemoglobins scavenge NO very effectively (Hausladen, A. et al., *Proc. Natl. Acad. Sci. USA* 95:14100–5 (1998); Gardner, P. R. et al., *J. Biol. Chem.* 273:26528–26533 (1998)), and, unlike human Hb, they do so enzymatically (Ioannidis, N. et al., *Biochem J.* 288: 649–655 (1992); Poole, R. K. et al, *Proc. R. Soc. Lond. Biol. Sci.* 255:251–8 (1994)). This gives HMP the potential to scavenge NO in therapeutic applications at substantially lower concentrations than Hb. Additionally, HMP can be regulated by provision of substrate, whereas the activity of oxyHb is indiscriminate. NO electrode assays have established that nanomolar concentrations of HMP can effectively eliminate NO in vitro. HMP's ability to counteract NO-dependent vasorelaxation in rabbit aorta has been investigated by a well-established method in which contractions or relaxations induced by various agents are recorded (Example 5). See Stamler, J. S. et al., *Proc. Natl. Acad. Sci. USA* 89:444–448 (1992).

Aortic rings preconstricted with phenylephrine (PE) show a slow relaxation over time. The fast relaxations after acetylcholine (ACh) addition to PE constricted vessels represent the classic endothelium derived relaxing factor (EDRF) dependent vasodilation, which are mediated by NO. FIG. 12A shows that purified HMP at concentrations as low as 1 nM caused noticeable long lived vasoconstriction in aortic segments in the presence of NADH, while in the absence of NADH, no constriction was observed. Sustained constriction, either of spontaneous or ACh induced relaxations, were only achieved when both NADH and HMP were present, demonstrating that HMP, when administered in a method of therapy, is capable of reversing NO induced hypotension, such as occurs in sepsis, and that the extent of vasoconstriction can be controlled by NAD(P)H. This is in contrast to the use of oxyhb as a method of therapy in sepsis, which is complicated by pulmonary hypertension, an undesirable side effect.

Another system has been established for the study of blood flow to tumors (Dewhirst, M. W. et al., *Radiat. Res.* 130:171–182 (1992); Dewhirst, M. W. et al., *Cancer Res.* 54:3333–3336 (1994); Foltz, R. M. et al., *Neurosurgery* 36:976–984 (1995)), which is partially dependent on NO. It is known that agents capable of reducing blood flow to tumors may be used to slow tumor growth, particularly in conjunction with chemotherapy. This model has been used to explore the use of HMP as a possible antitumor agent. FIG. 14 illustrates the application of this model. Human hemoglobin effectively reduces blood flow to tumors (FIG. 13), however, human hemoglobin has systemic side effects (causing increased blood pressure) and constricts blood vessels indiscriminately. In contrast to hemoglobin, HMP is an enzyme and can be regulated at lower concentrations by substrate. Selectivity can be achieved by local administration of substrate. Furthermore, HMP enzymatically generates $O_2^-$ to kill tumors once it has eliminated NO. HMP does not increase blood pressure but reduces flow in tumors (FIG. 14). HMP was used at 50–100 ng infused systemically.

The present invention also provides a method for treating or preventing an inflammatory condition in a mammal, comprising administering an effective amount of one or more types of a composition comprising flavohemoglobin. The inflammatory condition can be acute or chronic, and can include those inflammatory conditions associated with immune or autoimmune disorders, whether systemic or organ specific, and those inflammatory conditions associated with infections. Specific examples of conditions which may be treated or prevented in accordance with the present inventive method include, but are not limited to, rheumatoid arthritis, osteoarthritis, systemic lupus erythematosus, psoriasis, discoid lupus, collagen vascular disease, diabetes mellitus, myositis, polyarteritis, scleroderma, sarcoidosis, granulomatous lesions such as hepatic granulosa, inflammatory bowel disease, thyroiditis, multiple sclerosis, graft versus host disease, organ transplant rejection, sepsis, acute respiratory distress syndrome, myocardial infarction, stroke, cirrhosis, periodontitis, gingivitis, AIDS dementia, glomerulonephritis, hemodynamic compromise of shock and inflammation of the central nervous system.

Compositions comprising flavohemoglobin can also be administered for the treatment of diseases associated with dysregulation of blood flow, such as diabetic retinopathy, and cancer, wherein local constriction of blood vessels supplying tumors can starve tumors of oxygen.

Further applications for isolated flavohemoglobin protein or a composition comprising flavohemoglobin include the treatment of cancer. The local administration of flavohemoglobin into a tumor or in local proximity to a tumor can cause the constriction of blood vessels supplying blood to the tumor, thereby reducing the levels of oxygen and nutrients reaching the tumor cells. A further application of a composition comprising flavohemoglobin is in the local production of superoxide and other reactive oxygen species from $O_2$ in the absence of NO or biologically important carriers of NO such as S-nitrosothiols. Superoxide is highly reactive with functional groups in biomolecules and is a precursor of toxic oxygen species. Flavohemoglobin administered locally can serve to sensitize tumor cells to radiation therapy or chemotherapy by its activity of generating superoxide. The local administration of flavohemoglobin can be by injection through a needle or by implantation of a device to gradually disseminate a continual dose or multiple doses of flavohemoglobin, for example, an infusion pump. Flavohemoglobin or a composition comprising flavohemoglobin can be administered alone or in combination with other pharmaceuticals in antitumor therapy.

The dose administered to an animal or human, in the context of the present invention, should be sufficient to effect a prophylactic or therapeutic response in the animal over a reasonable time frame. One skilled in the art will recognize that the preferred dosage will depend on a variety of factors including the activity of the enzyme composition, the condition of the mammal, the body weight of the mammal, the severity of the inflammation, and where administration is to be local, the site to be treated. The size of the dose will also be determined by the possible side effects that might accompany the administration of the flavohemoglobin.

Suitable means of administration of isolated flavohemoglobin or a composition comprising flavohemoglobin include parenteral routes, particularly by intravenous injection. Administration can also be by injection into a local site of inflammation, as in a joint, or by inhalation, as for the treatment of ARDS. A composition comprising flavohemoglobin can be delivered or administered, for instance, by methods that are subcutaneous, intramuscular, intravenous, intradermal or in aerosol form. Some examples of local administration include injection into a muscle, tendon or cyst. Intraarticular injection or injection into a joint space may be preferred in certain cases of arthritis.

The present invention will now be illustrated by the following Exemplification, which is not intended to be limiting in any way.

EXEMPLIFICATION

Abbreviations: SNO, S-nitrosothiol; GSNO, S-nitrosoglutathione; SNO-Cys, S-nitrosocysteine; DEANO, diethylamine-NO; HMP, flavohemoprotein; NOS, nitric oxide synthase; SOD, superoxide dismutase; EDRF, endothelium-derived relaxing factor.

Methods for Examples 1–3

Mutant hemoglobin constructs. Cloning and characterization of *Ascaris* hemoglobin domain one (D1) and mutant D1 with the leucine substituted for B10 tyrosine (B10YL) have been described (Kloek, A. P., et al., *J. Biol. Chem.* 268: 17669–17671 (1993)). D1 with the serine substituted for A7 cysteine (A7CS) was generated by PCR using D1 cDNA as template with a synthetic forward primer containing the mutation (5'gcatccatggcgaataaaacgagagaac-tatccatgaaatcactcgaa 3') (SEQ ID NO: 1) and a synthetic reverse primer to the extreme 3' end of the gene as described (Kloek, A. P., et al., *J. Biol. Chem.*, 268:17669–17671 (1993)). A two-step PCR strategy was utilized to mutate each of the other two D1 cysteine residues to serines. D1 cDNA was used as template, and synthetic forward and reverse primers to the extreme 5' and 3' ends of D1 were as described. Synthetic mutant primers used in the first PCR step were as follows: D1 with E15 cysteine (residue 72) mutated to serine (E15CS) 5' ctcttggcaagccacgttctt 3' (SEQ ID NO: 2) and its complement; and, D1 with E19 cysteine (residue 76) mutated to serine (E19CS) 5' gcatgccacgttctttc-cgccacctacgatgac 3' (SEQ ID NO: 3) and its complement. Mutant D1 constructs were cloned into pET-8C as described (Minning, D. M., et al., *J. Biol. Chem.*, 270:22248–22253 (1995)).

Hemoglobin expression and purification. Native *Ascaris* hemoglobin (AH) was pelleted from the hemolymph of freshly obtained *Ascaris suum* (Carolina Biological Supply Co.) by ultracentrifugation at 80,000 g for 16 hours. Hemoglobin was further purified by fractionation on a Waters DEAE-5PW anion exchange column eluted with a linear gradient of 50 to 500 mM NaCl. Purified globins were >95% of all protein as assessed by SDS-PAGE.

Preparation of deoxy, ferric, and ferric-nitrosyl hemoglobin. Deoxy native *Ascaris* hemoglobin was obtained after incubation of AH(FeII)$O_2$ with sodium dithionite, for over 10 min. AH(FeII)$O_2$ (6 µM heme content) was incubated overnight in the presence of 50 µM potassium ferricyanide to completely oxidize hemes. In order to obtain AH(FeIII) NO, a final concentration of 18 µM NO was added to ferricyanide-oxidized AH. Spectra were recorded in a Perkin Elmer W/Vis Spectrometer, Lambda 2S. Heme content was assessed by the pyridine hemochromagen method (Antonini, E. & Brunori, M., *Frontiers in Biology*, 21 (1971)).

Titration of AH with NO. The concentration of NO saturated solutions varied between 1.2 and 1.8 mM. The concentration of NO in stock solutions was assessed by titrating NO against oxyhemoglobin and monitoring the change in absorbance at 630 nm. Nitric oxide from the stock solution was added sequentially by injection in a gas-tight Hamilton syringe with a Teflon seal to 1 ml AH (6 μM heme content in phosphate buffer saline (PBS), pH 6, in the presence or absence of 500 μM NADPH. Spectra were immediately recorded after each addition of NO.

NO metabolism. A Clark type NO electrode (Iso-NO, World Precision Instruments) immersed in a stirred glass vial was used to measure NO consumption. NO was added at a final concentration of 6 μM to AH (1.5 μM heme content) in PBS, pH 6, in the presence or absence of 500 μM NADPH. In order to determine end products of NO metabolism, varying amounts of the NO donor, diethylamine-NO (DEANO), were added to AH (1.5 μM heme content) with 500 μM NADPH in PBS, pH 6. Samples were assayed for nitrite and nitrate by the Greiss reaction and high performance capillary electrophoresis (Applied Biosystems) (Hausladen, A., et al., *Proc. Natl. Acad. Sci. USA*, 95:14100–14105 (1998)).

S-nitrosylation of hemoglobins. Transnitrosation of globins was carried out as previously described (Jia, L., et al., *Nature*, 380:221–226 (1996)). Globins were incubated in the presence of 2- to 10-fold excess S-nitrosocysteine in 10% v/v borax, 100 μM diethylenetriaminepentaacetic acid (DTPA), pH 9. S-nitroso groups (SNO) and nitrosyl hemes (Fe—NO) were measured by photolysis chemiluminescence in the presence and absence of a six-fold molar excess of $HgCl_2$ (U.S. Pat. No. 5,891,735; Gow, A. J. & Stamler, J. S., *Nature*, 391:169–173 (1998)).

Kinetic analysis of AH. An Applied Photosystems stopped-flow spectrophotometer was utilized for kinetic studies of AH. Spectra were collected from 350–750 μm. AH was used at a final concentration of 6 μM heme content, with 25 μM DEANO in the presence or absence of 500 μM NADPH. Solutions were deoxygenated by bubbling with argon for 45 min. Data were analyzed using Pro-K software for the SX.18MV.

Oxygen consumption. 2 ml of PBS, pH 6, was placed in a sealed glass vessel in which a Clark electrode was situated. NADPH, NO, or AH could be added by injection through a capillary opening by means of a gas tight syringe. Data were collected by means of an analogue chart recorder.

EXAMPLE 1

*Ascaris* Hemoglobin: A Nitric Oxide-Activated Deoxygenase

Figure 1A:
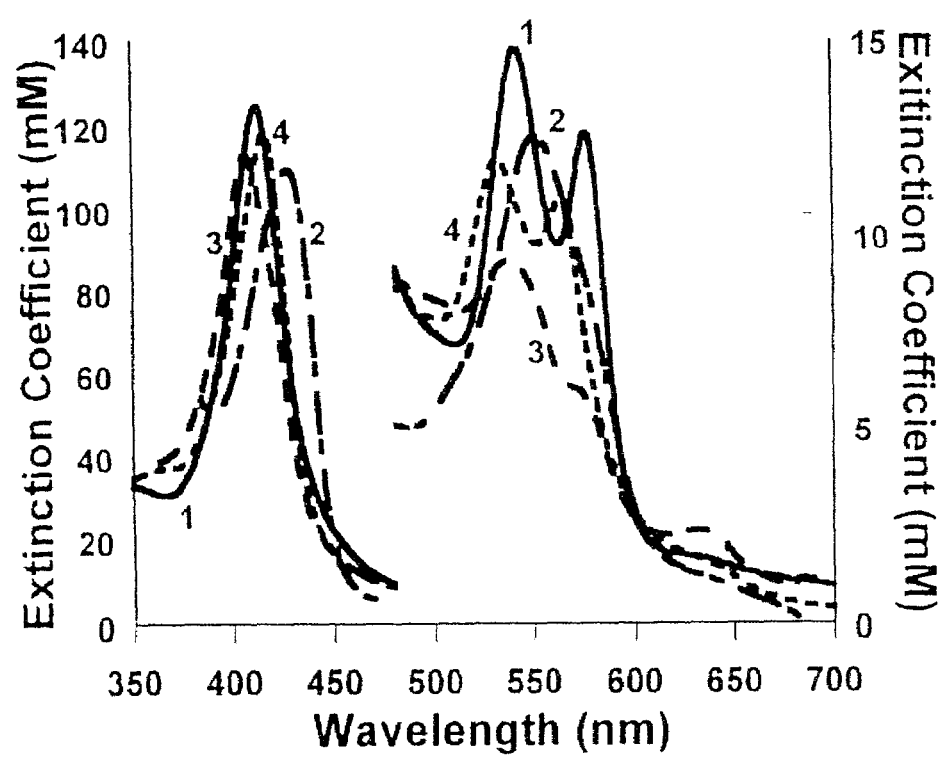
FIG. 1A shows the absorption spectra of purified Ascaris hemoglobin (AH). AH purified from the perienteric fluid of fresh worms was >95% (FeII)$O_2$ (spectrum 1, solid line). AH(FeII)$O_2$ has a peak in the Soret region at 412 nm and peaks in the visible spectrum at 542 and 577 nm. Deoxygenation of AH was achieved by incubation with dithionite. AH(FeII) (spectrum 2, short-long dashed line) has a Soret peak at 428 nm and a visible peak at 550 nm. Ferricyanide treatment of AH resulted in AH(FeIII) (spectrum 3, long dashed line), which has a Soret peak at 407 nm and peaks at 539 and 573 nm in the visible range. A characteristic peak at 630 nm is also present. NO was added to AH(FeIII) to obtain AH(FeIII)NO (spectrum 4, short dashed line), which has a Soret peak at 416 nm and peaks in the visible region at 532 and 564 mn.
Figure 1B:
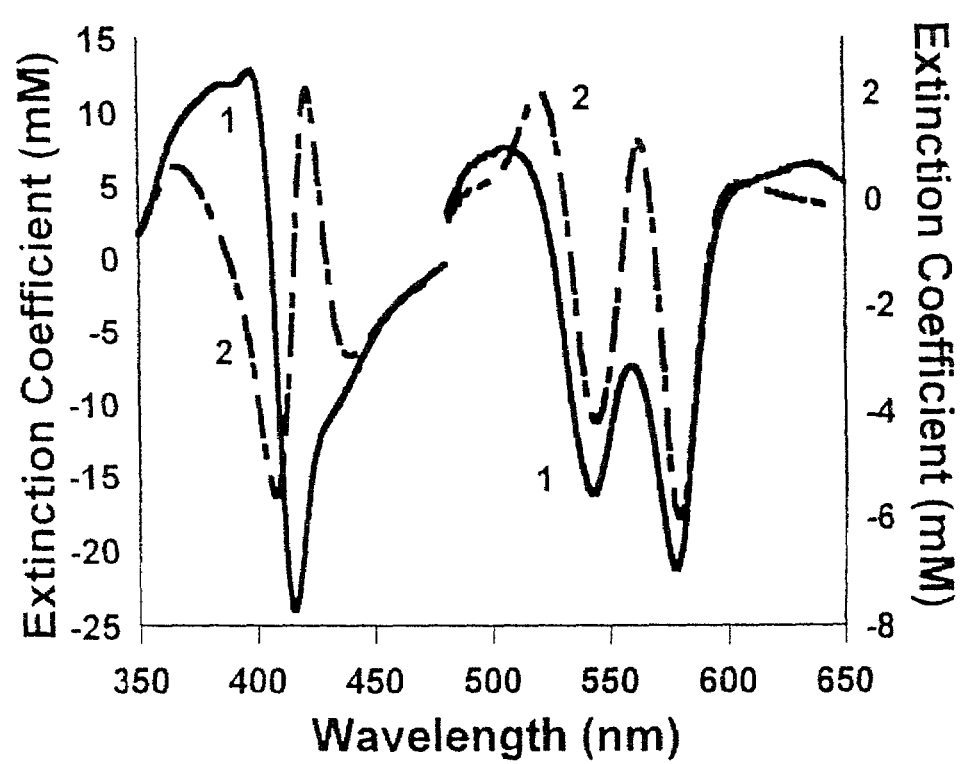
FIG. 1B shows difference spectra for various forms of AH. The difference spectrum of AH(FeIII) versus AH(FeIII)$O_2$ (spectrum 1, solid line) demonstrates a shift in the Soret region to the left, with a maximum at 398 nm and minimum at 416 nm. The visible region is characterized by a reduction in absorbance, with a peak at 507 nm and an increase at 630 nm. AH(FeIII)NO versus AH(FeII)$O_2$ (spectrum 2, dashed line) has a shift in the Soret region to the right, with a peak at 422 nm. There is a reduction throughout the visible region, with peaks at 521 nm and at 563 nm.
Figure 1C:
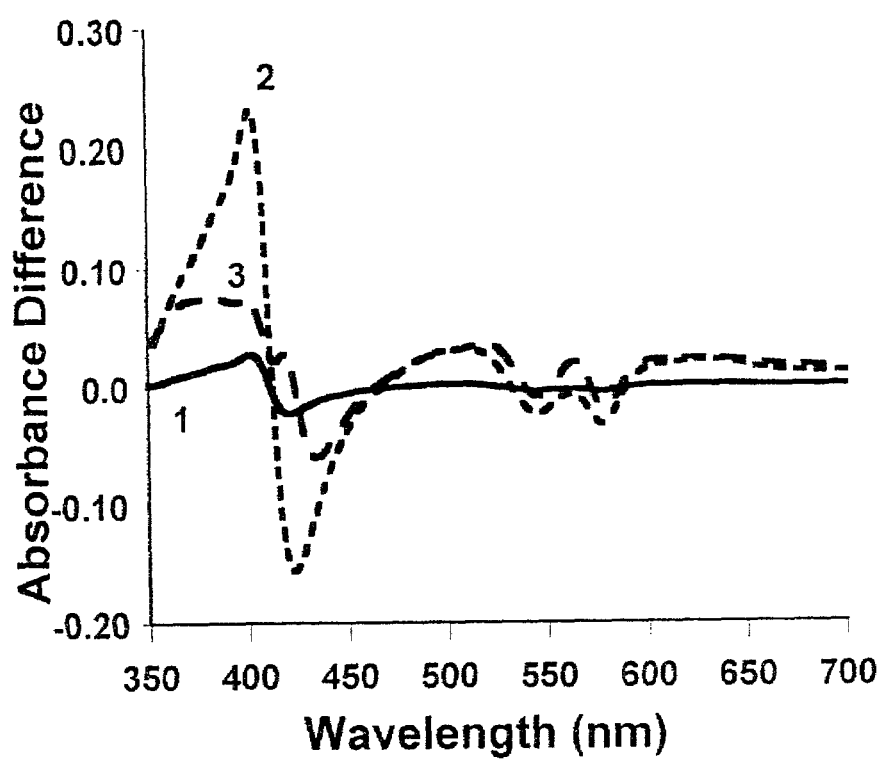
FIG. 1C shows difference spectra recorded while titrating AH with NO in the absence of NADPH. Repeated additions of NO (aq) (1.8 µM, each) were made to AH (6 µM heme content). Spectra were recorded immediately after mixing. Results are shown as difference spectra against AH(FeII)$O_2$. Initial addition of NO resulted in the rapid appearance of a small amount of AH(FeIII) (spectrum 1, solid line) as seen by an increase in absorbance at approximately 400 nm. A peak AH(FeIII) difference spectrum was observed after 11 additions of NO (19.8 µM) (spectrum 2, short dashed line). Subsequent additions of NO up to 45 µM resulted in the buildup of AH(FeIII)NO (spectrum 3, long dashed line), detected by the appearance of a small peak at 418 and 519 nm, along with an increase at 563 nm.
Figure 1D:
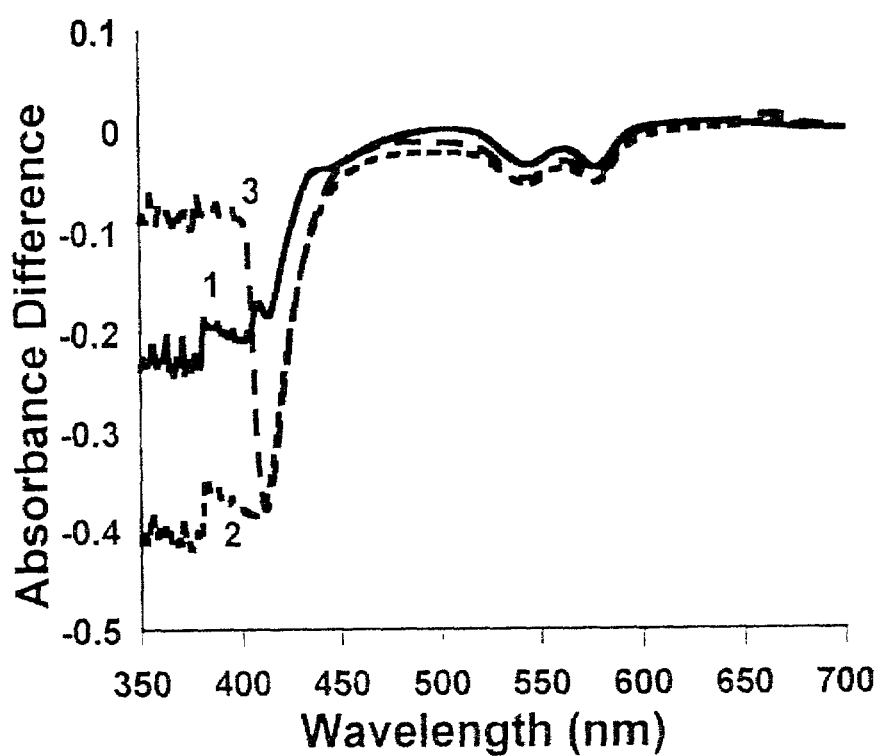
FIG. 1D shows difference spectra recorded while titrating AH with NO in the presence of NADPH. The experimental procedure described for FIG. 1C was repeated in the presence of 500 µM NADPH. Initial addition of NO resulted in the appearance of a greater amount of AH(FeIII) (spectrum 1, solid line). A peak AH(FeIII) spectrum was observed after only 8 additions (14.4 µM) (spectrum 2, short dashed line). Additions of NO totaling 45 µM, yielded AH(FeIII), with no detectable AH(FeIII)NO (spectrum 3, long dashed line). These data suggest that in the presence of cofactor NADPH, AH effectively consumes NO.

Extinction coefficient spectra for variously liganded and oxidized forms of AH were constructed, from which difference spectra were derived (FIGS. 1A and 1B). Absorption-difference spectroscopy was then used to examine the reaction of NO with AH. NO was titrated against 6 μM AH (heme content) in 1.8 μM steps. Addition of NO resulted in the immediate formation of methemoglobin (FIG. 1C). whereas oxidation by ferricyanide (Davenport, H. E., *Proc. R. Soc. London Ser. B*, 136:355–270 (1949)), which requires dissociation of liganded oxygen takes place, in AH, over many minutes. The peak ferric heme yield was seen after addition of 19.8 μM NO, i.e., with a concentration of NO that far exceeds the concentration of heme (FIG. 1D). Further additions of NO, to a total of 45 μM, induced the accumulation of AH(FeIII)NO with the consumption of $O_2$.

Taken together, these data suggest that NO is directly oxidizing AH(FeIII)$O_2$ to methemoglobin (equations (5) and (6)), that NO reacts with metAH to form AH(FeIII)NO (equation (7)), and that additional reactions must be occurring.

$$AH(FeIII)O_2 \Longleftrightarrow AH(FeIII)O_2^- \tag{5}$$

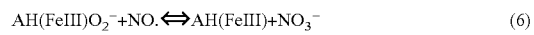

$$AH(FeIII)O_2^- + NO. \Longleftrightarrow AH(FeIII) + NO_3^- \tag{6}$$

$$AH(FeIII) + NO. \Longleftrightarrow AH(FeIII)NO \tag{7}$$

Photolysis-chemiluminescence was employed to measure the NO content of 6 μM AH following the stepwise addition of 45 μM NO as described above. The analysis detected 7.8 μM NO in AH, of which 65% (5.1 μM) was S-nitrosothiol (AH—SNO). These data are consistent with the existence of an equilibrium that is known to occur between Fe(III)NO in mammalian hemoglobin and SNO (equation (8)), but fundamental questions remain. First, the transfer of NO$^+$ from heme to thiol in AH would be inevitably coupled to binding of oxygen (equation (9)), which was not detected. Second, NO mass balance is still unaccounted for. That is, most added NO did not form either a chemiluminescence-detectable or spectrally active nitrosyl species.

$$AH(FeIII)NO+(cys)S^- \Longleftrightarrow AH(FeII)+(cys)SNO \tag{8}$$

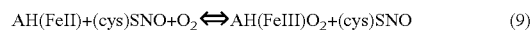

$$AH(FeII)+(cys)SNO+O_2 \Longleftrightarrow AH(FeIII)O_2+(cys)SNO \tag{9}$$

Accordingly, NO might be consumed in a reaction with oxygen to form nitrate (equation (10)); however, this would require a source of electrons (equation (11)).

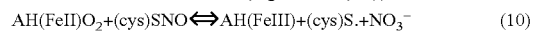

$$AH(FeII)O_2+(cys)SNO \Longleftrightarrow AH(FeIII)+(cys)S.+NO_3^- \tag{10}$$

$$AH(FeIII)+(cys)S.+e^- \Longleftrightarrow AH(FeIII)+(cys)S^- \tag{11}$$

Previous work has revealed that AH is capable of reducing oxidized cytochrome c in an NADPH-dependent fashion (Sherman, D. R., et al., *Science*, 258:1930–1932 (1992)). The above titration was repeated with NADPH present (FIG. 1D). NADPH was found to increase the efficiency with which AH was oxidized by NO. Specifically, a peak in AH(FeIII) yield was seen with only 14 μM NO. More significantly, minimal AH(FeIII)NO (1.6 μM) and no AH—SNO were detected, even after addition of 45 μM NO (compared with 6 μM heme content). The lack of accumulation of either AH(FeIII)NO or AH—SNO in the presence of NADPH suggests that AH metabolized NO in an NADPH-dependent manner, The NO/SNO complexes that build up in the absence of substrate NADPH are probably reaction intermediates.

Figure 1E:
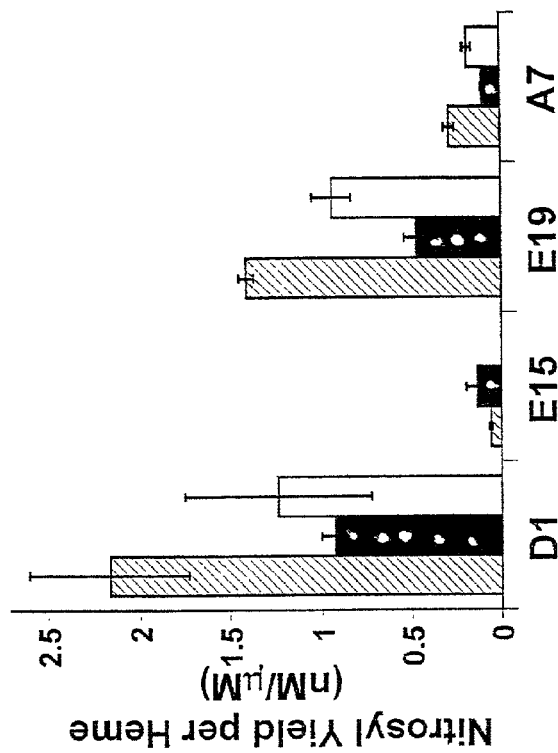
FIG. 1E is a graph showing the total nitrosyl content of various forms of AH after transnitrosation in the presence or absence of NADPH. Under conditions favoring selective transnitrosation of thiols (Jia, L. et al., Nature 380:221–226 (1996)), incubation of AH (178 µM heme content) with S-nitrosocysteine (2-fold molar excess over heme) in the absence of NADPH lead to rapid oxidation of the heme (data not shown). Photolysis-chemiluminescence was used to measure yields of total nitrosyl content of AH (striped bars), AH(FeIII)NO (solid bars), and AH—SNO (open bars). The same procedure was repeated in the presence of 500 µM NADPH, yielding oxidation of the heme moiety (not shown), but with drastically reduced quantities of total nitrosyl content, AH(FeIII)NO and AH—SNO, indicative of NO metabolism (not shown).

Analysis of fresh *Ascaris* perienteric fluid revealed the presence of endogenous SNO (approximately 5% relative to heme content, data not shown). Incubation of AH with S-nitrosocysteine under conditions that selectively S-nitrosylate human hemoglobin (Jia, L., et al, *Nature*, 380:221–226 (1996)), produced AH—SNO (FIG. 1E). However, the hemes in AH were rapidly oxidized by S-nitrosocysteine, and significant amounts of heme-bound NO were detected. This differs from human hemoglobin, where little heme oxidation is observed (Jia, L., et al., *Nature*, 380:221–226 (1996)). As might be predicted from equations 8–10, levels of heme-bound NO and AH—SNO were significantly reduced by addition of NADPH, and moreover, nitrate ($NO_3^-$) accumulated in reaction mixtures (see more below). Coupling of heme and thiol in NO reactions was further suggested by studies of a mutant of the first heme domain (D1), which is oxidized by the substitution of B10 tyrosine to leucine. Treatment with S-nitrosocysteine resulted in the formation of D1-SNO and in reduction of the hemes. These data as a whole suggest that thiol(s) and heme(s) in AH are redox partners that transfer NO and/or electrons, and that NO is metabolized in these reactions.

Figure 1F:
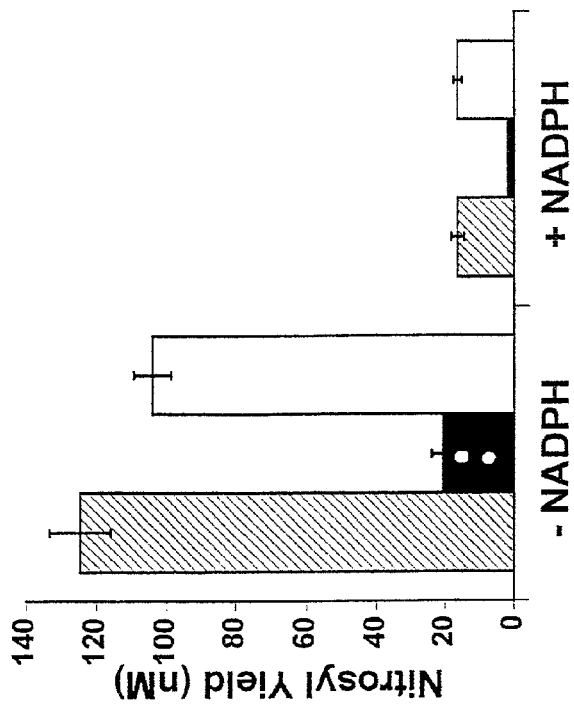
FIG. 1F is a graph showing that the A7, E15 and E19 cysteine residues of AH are nitrosylated and participate in NO reactions. S-nitrosylation of recombinant D1 and of D1 mutants, with serines substituted for cysteines (A7, E15, and E19), was performed with 10-fold molar excess S-nitrosocysteine, and otherwise as described in FIG. 1E. For comparison, results were standardized against heme content; total nitrosyl content (striped bars), and SNO (open bars) contents are shown. These data indicate that the heme, E15 and A7 cysteines, and, to a lesser extent, E19 cysteine, can form a redox system allowing for intramolecular transfer of electrons and/or NO.

The first globin fold, D1, contains three cysteine residues (A7, E15, and E19) that are conserved in the second globin fold, D2 (albeit D2 and intact AH have not been cloned). In order to assess involvement of these thiols in AH function, the effects of S-nitrosylation of recombinant D1 and mutants in each of the three cysteine residues were examined (FIG. 1F). Treatment with S-nitrosocysteine induced oxidation of native D1 and all of the mutants. Mutation of the E19 cysteine, located in the proximal heme pocket (analogous to human Cysβ93), had only a modest effect on the formation of both S-nitrosothiol and heme-bound NO. In contrast, mutation of the E15 cysteine, which lies in close proximity to the ligand binding site (Darawshe, S., et al., *Biochem. J.,* 242:689–694 (1987)), blocked SNO formation, as well as subsequent production of heme-bound NO. E15 cysteine thus has a critical role in heme-thiol interactions. NO was inefficiently captured by the E15 thiol, in the A7 mutant. These observations are consistent with a model of initial capture of $NO^+$ by the surface A7 cysteine, followed by intramolecular transfer of the NO group to internal thiols, most notably E15 cysteine, and then to heme. The design of the distal pocket may facilitate interaction between the dioxygen bound to the heme and NO bound to E15 thiol, forming a peroxynitrosyl intermediate that then rearranges to nitrate (equations (12) and (13)).

$$AH(FeII)O_2 + SNO(E15cys) \Leftrightarrow AH(FeII)OOONS(E15cys) \quad (12)$$

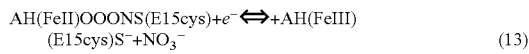

$$AH(FeII)OOONS(E15cys) + e^- \Leftrightarrow +AH(FeIII)(E15cys)S^- + NO_3^- \quad (13)$$

NO was added to AH in solution to test the possibility that it is enzymatically consumed. NO levels were directly monitored via an electrochemical probe. AH reduced the level of NO as compared to its concentration in AH-free solutions (FIG. 2A). This reduction was approximately equivalent to the concentration of heme present (1.5 μM heme, 1.9–2.1 μM NO reduction), indicating a single round reaction of NO with AH $(FeIII)O_2$. In these experiments performed in the absence of NADPH, the rate of NO decay matched that observed in buffer. In contrast, NO decay by AH was accelerated more than 10-fold in the presence of NADPH. Thus, AH enzymatically metabolizes NO in an NADPH dependent manner.

Stopped-flow spectrophotometry was utilized to gain further insight into the mechanism of NO consumption by AH. The addition of 25 μM NO to 6 μM AH in the absence of NADPH (FIGS. 2B and 2C), resulted in the rapid formation of AH(FeIII) (observed initial rate 888 nMs$^{-1}$), followed by a buildup of AH(FeIII)NO (observed rate 26 nMs$^{-1}$). AH(FeIII)NO was formed prior to complete oxidation of AH(FeIII)$O_2$. Addition of 500 μM NADPH, slowed the NO induced conversion of AH(FeIII)$O_2$ (FIGS. 2D and 2E) to AH(FeIII) (observed initial rate 290 nMs$^{-1}$), but increased the yield of oxidized AH and prevented detectable AH(FeIII) NO from forming. The slower build up of AH(FeIII) in the presence of NADPH and the early detection of AH(FeIII) NO in its absence, suggests that AH(FeIII) is competitive with AH(FeIII)$O_2$ for NO. Previous work on other globins demonstrated that replacement of the distal histidine with glutamine increased reactivity of heme iron with NO by 1000-fold (Sharma, V. S., et al., *Biochem.,* 26:3837–3843 (1987); Sharma, V. S., et al., *Biochem.,* 22:3897–3902 (1983)). The reduced rate of AH(FeIII) formation in the presence of NADPH is most likely a result of NO turnover, i.e. the observed rate is the combination of AH(FeIII) production and consumption.

The products of NO consumption by AH were determined using the NO donor diethylamine NONOate (DEANO). In control studies, 5 μM DEANO released NO over 2 min (FIG. 2F). When AH was present, however, NO was undetectable electrochemically. That is, AH metabolized NO. Varying amounts of DEANO (1–8 μM, yielding 2–16 μM NO) were incubated in NADPH solutions with and without AH (1.5 μM heme content) and the products were analyzed for nitrite and nitrate (Table 1). In the absence of AH, 1.5 μM DEANO resulted in no detectable nitrite or nitrate, presumably due to loss of NO to the atmosphere. However, in the presence of AH, NO was effectively captured and fixed as nitrate. Upon addition of increasing amounts of DEANO, solutions containing AH metabolized NO primarily to nitrate, whereas in the absence of AH, nearly equimolar levels of nitrite and nitrate were observed. AH transformation of NO to nitrate was seen even under very low oxygen tension (not shown). Taken together, these data clearly implicate an enzymatic function for AH in metabolizing NO and oxygen to produce nitrate.

TABLE 1

| Concentration of DEANO added (mM) | $NO_2^-$ (mM) −AH | $NO_3^-$ (mM) −AH | $NO_2^-$ (mM) +AH | $NO_3^-$ (mM) +AH |
|---|---|---|---|---|
| ~2 | 0.01 ± 0.088 | 0.01 ± 0.682 | 0.01 ± 0.274 | 1.20 ± 0.108 |
| ~4 | 0.77 ± 0.042 | 1.00 ± 0.120 | 0.06 ± 0.175 | 8.52 ± 0.120 |
| ~8 | 5.69 ± 0.520 | 8.13 ± 0.271 | 2.44 ± 0.067 | 11.64 ± 0.286 |

End product analysis of NO metabolism by AH. Varying amounts of DEANO were added to solutions containing 500 μM NADPH with or without AH (1.5 μM heme content). Yields of nitrite and nitrate were determined by both the Greiss reaction and high performance capillary electrophoresis. Values are the mean ± standard error for three experiments.

Consumption of oxygen by AH was examined with a Clark electrode in a sealed vessel (FIG. 3A). Incubation of purified AH protein with NADPH caused a reduction in oxygen tension even in the absence of NO. The visible spectrum of oxygen ligated AH did not change with decreasing oxygen tension, in keeping with its high avidity for oxygen. In fully deoxygenated buffer, however, the protein was converted to the deoxy form by NADPH (FIG. 3B). Thus, AH exhibits intrinsic NADPH oxidase activity. The addition of NO to the vessel, moreover, resulted in a rapid acceleration of oxygen consumption. The total oxygen consumed upon addition of 10 μM NO to the reaction mixture was approximately 43 μM. Even taking into account a background rate of oxygen consumption, this corresponds to a ratio of at least two oxygen molecules per NO. NO addition to AH, prior to NADPH, which would enable the build up of AH(FeIII)NO, completely inhibited oxygen consumption.

EXAMPLE 2

AH Reduces Oxygen Tension in the Perienteric Cavity of *Ascaris,* and in the Intestines of Infected Hosts.

The oxygen tension in the intestines of swine infected with *Ascaris suum,* and the oxygen and NO content of the perienteric fluid of worms (*Ascaris suum*) exposed to oxidative stress were measured. *Ascaris* can migrate throughout the gut of swine, but predominantly reside in the jejunum.

Forty measurements of jejunal $pO_2$ were made using two pigs. The measured jejunal $pO_2$ ranged from 0 to 10 mm Hg, with an apparent $O_2$ gradient from the intestinal wall (~10 mm Hg) to the lumen (~0 mm Hg). Eleven worms were isolated from pig intestines. A cannula was inserted into the perienteric cavity of three of the worms. For each worm, the cannula was inserted ~1 cm below the head, and a fiber optic $O_2$ probe was inserted through the cannula. When the worms were exposed to oxidative stress, the $pO_2$ of the cavity consistently remained at 4 mm Hg (FIG. 5A). A second cannula was inserted into the perienteric cavity, and the cavity was drained of the AH-containing perienteric fluid. After the perienteric fluid was drained, the cavity $pO_2$ increased to ~40 mm Hg (FIG. 5A).

The perienteric fluid of individual freshly isolated adult female Ascaris worms was collected and analyzed for SNO and FeNO content by photolysis-chemiluminescence. The freshly collected perienteric fluid contained 6.15±0.37 µM bound NO (1–2 NO per octamer AH), which was present as SNO and metal nitrosyl (FeNO) (FIG. 5B). Moreover, the amount of SNO in perienteric fluid was inversely correlated with metal nitrosyl content, consistent with functional coupling between heme and thiol (Equation (8)).

The data demonstrate that AH is a nitric oxide-activated deoxygenase that can utilize endogenously produced NO to detoxify oxygen.

EXAMPLE 3

Myoglobin Catalyzed Deoxygenation

Myoglobin (from human heart; Sigma, St. Louis, Mo.) was added to aerated phosphate buffered saline at room temperature at a final concentration of 5 µM. Oxygen consumption was initiated by addition of 200 µM –1 mM NADPH or NADH. The reaction was followed with a Clark electrode in a sealed vessel. The rate of oxygen consumption by myoglobin was further accelerated dramatically by the addition of 1 to 25 mM NO. Addition of NO alone (i.e., without NADPH or NADH) had little effect upon oxygen consumption. The results are shown in FIG. 6.

From these data, a model for the consumption of $O_2$ myoglobin was constructed, which is presented herein as an illustration and is not intended to be limiting.

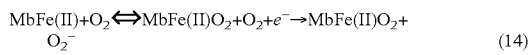
(14)

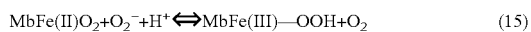
(15)

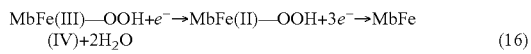
(16)

(17)

Methods for Example 4

Culture

Growth of Escherichia coli strain RK4936 in minimal medium, harvest of cells and lysis were as described (Hausladen, A. et al., Cell 86:719–729 (1996)). Strains YMC10 (wild type) and RB9060 (Δgln, Δhmp) (Liu, J. & Magasanik, B., J. Bacteriol., 175:7441–7449 (1993)), were provided by Dr. A. Ninfa, University of Michigan. The HMP overproducing strain AN1459/pPL757 was provided by Dr. N. E. Dixon, Australian National University; (Love, C. A. et al., Gene, 176:49–53 (1996)). To induce HMP, cells were grown from an overnight culture (1% inoculum) to an $A_{600}$ of 1.0 and then diluted 50-fold into fresh medium. When the $A_{600}$ had reached 0.2, cells were treated with 0.2 mM S-nitrosocysteine (SNO-Cys) and grown for an additional 90 min. The cells were harvested by centrifugation for enzyme purification. To test for inducible resistance, the pretreated cells were diluted (to an $A_{600}$ of 0.1) into fresh, prewarmed medium and rechallenged with 0.2 with 0.2 mM SNO-Cys. Cell density was then recorded every 15 min for 2 hr. For HMP purification, strain AN1459/pPL757 was grown from an overnight culture (2% inoculum) at 30° C. in 4 liters LB medium/50 µg/ml ampicillin to an $A_{600}$ of 0.5 and then supplemented with 1 mM a-aminolevulinic acid, 1 mM ATP and 100 µM riboflavin, (Martasek, P. et al., Biochem. Biophys. Res. Commun. 219:359–365 (1996); Seo, H. G. et al., Biochem. Biophys. Res. Commun. 208:10–8 (1995)). The temperature was then shifted to 42° C. and the cells were grown for an additional 6 hr in the dark. After harvest by centrifugation, the cell pellet was stored at –20° C.

SNO and NO Metabolism

A Clark type NO electrode (Iso-NO, World Precision Instruments) immersed in a stirred glass vial was used to measure NO released or consumed by bacteria or proteins. Cells were suspended in 2 mL minimal medium to an $A_{600}$ of 1.0. SNO—Cys or an anaerobic solution of NO was then added at final concentrations of 100 µM and 5 µM, respectively. NO consumption by column fractions or purified HMP were measured in 20 mM BisTrisPropane, pH 7.0 in the presence of 0.1 mM NADH. For measurement of the aerobic end products of NO reactions, either the NO donor diethylamine-NO (0.1 mM) or NO solutions were added to sealed vials that were filled to capacity (i.e., contained no headspace). The solution was then assayed for nitrite and nitrate by the Griess reaction (Schmidt, H. H. H. W. & Kelm, M., in Methods in Nitric Oxide Research (eds. Feelisch, M. & Stamler, J. B.). 491–497 (Wiley, Chichester, England 1996)), and/or simultaneously for nitrite and nitrate by capillary electrophoresis using a 75 µm×100 cm CE-select amine capillary (Supelco) at 20 kV. The capillary was periodically recoated with amine regenerator solution (eCAP, Beckman). GSNO decomposition was followed by the Saville reaction (Stamler, J. B. & Feelisch, M., in Methods in Nitric Oxide Research (eds. Feelisch, M. & Stamler J. B.) 521–539 (Wiley, Chichester, England 1996) or by decreases in absorbance at 340 nm. $N_2O$ measurements were performed on the headspace of sealed vials filled to 50% capacity by GC-MS (Arnelle, D. R. & Stamler, J. B. Arch. Biochem. Biophys. 318:279–285 (1995)). To screen for SNO-lyase and NO-metabolizing activity, column fractions were treated with 0.1 mM SNO—Cys or 10 µM NO and assayed for $NO_x^-$ production and the ability to accelerate NO breakdown. Oxygen consumption was measured with a Clark electrode (Yellow Spring Instruments) in a thermostated cell without headspace.

Enzyme Purification

Soluble extracts in 20 mM BisTrisPropane, pH 7.0, obtained after centrifugation at 100,000 g, were separated a MonoQ HR 10/10 column (Pharmacia), with a linear gradient from 0–1 M NaCl and assayed for SNO-lyase and NO consumption activities. Crude extracts from the HMP overproducing strain were treated with 100 µM hemin and 1 mM DTT and then applied to a 2.5×70 cm column of Q Sepharose FF (Pharmacia) and separated with a linear gradient of 0–0.5 M NaCl. Fractions exhibiting an intense brown color were >95% pure HMP as judged by SDS gel electrophoresis.

EXAMPLE 4

Demonstration of Catalytic Activity of Flavohemoglobin

The hypothesis that SNO is homolytically cleaved to NO by cells was tested. FIG. 7A shows that cells suspended in growth medium significantly increased the rate of NO release from SNO over growth medium alone. Heat and diamide inhibition of the reaction in cellular extracts provided additional evidence for an enzymatic lyase activity. However, the rate of NO decomposition by suspended cells did not obey the third order kinetics of autooxidation. Rather, the cells accelerated NO decay. This NO metabolizing activity was markedly increased in cells that had been pretreated with SNO (FIG. 7B). That is, the metabolic activity was inducible. Complementary studies with extracts showed that NO transformation was NADH dependent. It has been previously shown that OxyR exerts control over the metabolic fate of SNO and that a mutant strain is highly sensitive to SNO-induced cytostasis (Hausladen, A. et al., Cell 86:719–729 (1996)). However, both the constitutive SNO-lyase (SNO→S+NO) and inducible NO-metabolic activities were present in OxyR deficient cells (not shown). Taken together, these results are consistent with OxyR-independent pathways that cleave SNO to NO, metabolize NO, and generate nitrate.

To purify and characterize enzymes, chromatographic fractions from extracts of SNO treated and untreated cells were screened for SNO-lyase and NADH-dependent NO-metabolic activities. Anion exchange chromatography separated three major peaks with SNO-lyase activity (FIG. 7C), and one peak with the NO-metabolizing activity. This fraction also catalyzed the NADH-dependent decomposition of GSNO.

$$NADH+2GSNO+H^+ \rightarrow N_2O+GSSG+NAD^++H_2O \quad (18)$$

The NO and GSNO consumption activities were low in extracts from untreated cells, but strongly induced by SNO treatment (not shown). The chromatographic fraction containing the activities exhibited a distinctive hemoglobin spectrum following SNO exposure (FIG. 7D). E. coli possesses a flavohemoglobin (HMP) of unknown function that is reportedly induced by NO (Poole, R. K. Ioannidis, N & Orii, Proc. R. Soc. Lond. B. Biol. Sci., 255:251–258 (1994); Poole, R. K. et al. Microbiology 142:1141–1148 (1996), Poole, R. K. et al., Microbiology 143:1557–1565 (1997); Poole, R. K. et al., J. Bacteriol., 178:5487–5492 (1996)). Further purification of the hemoprotein by SDS gel electrophoresis, assays for ferric reductase activity (Eschenbrenner, M. et al., Biochem. Biophys. Res. Commun., 198:127–131 (1994)), and studies of an HMP deficient mutant, identified the NO/GSNO metabolizing activities with HMP. In particular, extracts from the HMP mutant were unable to catalyze NADH-dependent NO consumption (FIG. 8A), and HMP deficiency markedly increased susceptibility to SNO-induced cytostasis and severely compromised the inducible resistance to nitrosative stress (FIG. 8B).

HMP also exerted control on SNO and NO metabolism. Cells pretreated with SNO under aerobic conditions produced increased nitrate and less nitrite from SNO and NO, and this metabolic shift away from nitrite was HMP dependent (Table 2). Interestingly, the amount of $NO_x$ (i.e. nitrite+nitrate) recovered could not account for the SNO (and to a lesser degree NO) added, suggesting the existence of an additional (reductive) route of (S)NO decomposition that is, at least partly, HMP independent. In E. coli, it appears that multiple constitutive activities mediate SNO breakdown, among which are several lyase that generate NO. However, the HMP aerobic-metabolism pathway for SNO and NO is essential for acquisition of resistance to nitrosative challenge.

TABLE 2

HMP induction increases yield of nitrate in vivo.
Cells were either pretreated or not pretreated with 200 µM SNO-Cys and then exposed to either 200 µM SNO-Cys or diethylamine-NO. After 90 minutes, the growth medium was analyzed for nitrite and nitrate by capillary electrophoresis.

| Cells | Nitrite (µM) | Nitrate (µM) |
|---|---|---|
| No pretreatment | | |
| wild type | | |
| (SNO-Cys) | 77 | 6.6 |
| Δhmp | | |
| (SNO-Cys) | 98 | 1.9 |
| SNO pretreatment | | |
| wild type | | |
| (SNO-Cys) | 65 | 35 |
| (DEANO) | 143 | 22 |
| Δhmp | | |
| (SNO-Cys) | 90 | 3.7 |
| (DEANO | 161 | 3.1 |

HMP purified from an overexpressing strain was used to elucidate the mechanism of NO/GSNO breakdown. The protein exhibited the same NO (FIG. 9A) and GSNO (FIG. 10A) metabolic activities that we had isolated from wild type cells. The picture that emerged from spectroscopic studies and analyses of substrate utilization indicated that $O_2$ is bound to the heme during aerobic NO turnover (FIGS. 9B, 9C). Moreover, a nitrosylheme that was formed anaerobically did not turn over, and the NO ligand was rapidly replaced by $O_2$ (FIG. 9B). Thus NO transformation by the heme domain was only seen with $O_2$ bound. Cyanide significantly inhibited NADH oxidation and attenuated NO consumption, indicating that the site of NO reaction is the oxyheme (FIG. 9D). Product determinations under conditions where HMP maintained the steady state NO concentration below 50 nM revealed that HMP oxidized NO to nitrate ($NO_3^-$) and to some degree, nitrate ($NO_2^-$) (FIG. 9E). Only small amounts of $N_2O$ were detected and SOD did not influence product yields. SOD would have been expected to modify NO/superoxide reactions that generate nitrate. Measurements of oxygen consumption revealed that rates doubled in the presence of NO, and that one molecule of oxygen was consumed per molecule of NO (FIG. 9F). Taken together, the results indicate that the heme in bacterial hemoglobin functions as an oxygenase. While not wishing to be bound by a particular mechanism, a reaction mechanism is proposed wherein NO binds to $Fe(II)O_2$, forming a nitrosyldioxyl complex (Fe[II]—O—O—N=O). Release of nitrate then leaves an Fe[III]. Alternative production of nitrite might be explained by the reaction of NO with the OONO intermediate (Equation 20) (D. A. Wink, et al., J. Biol. Chem., 272:11147–11151(1997)). In either case, electrons from NADH reduce the oxidized iron, regenerating the ferrous heme. A new round of catalysis is then initiated by $O_2$ binding to heme (Equation 21), which has been shown to occur very rapidly and with high affinity (R. K. Poole, et al., Microbiology, 142:1141–1148 (1996)).

$$HMP(FeII)O_2 + NO \rightarrow HMP(FeIII) + NO_3^- \qquad \text{Equ. 19}$$

$$HMP(FeIII)^{\delta+}OONO^{\delta-} + 2NO \rightarrow HMP(FeIII) + NO_2^- + N_2O_3 \qquad \text{Equ. 20}$$

$$HMP(FeIII) + O_2 + 0.5 NADH \rightarrow HMP(FeII)O_2 + 0.5 NAD^+ \qquad \text{Equ. 21}$$

Several lines of evidence indicated that the mechanism of GSNO decomposition was different from that of NO. First, GSNO turnover was largely unaffected by cyanide (FIG. 10A) and did not increase oxygen consumption in the presence of NADH (FIG. 10B). Moreover, GSNO was broken down efficiently under aerobic conditions, while NO was not. These results excluded involvement of either the heme or $O_2$ in the reaction mechanism. Second, GSNO increased NADH oxidation more so than NO (FIG. 10C). Third, $N_2O$ and oxidized gluthathione were major reaction products, whereas only small amounts of nitrite and nitrate were formed (FIG. 10D) and reduced glutathione was not detected either aerobically or anaerobically. 60–70% of substrate thiol was transformed into GSSG under anaerobic conditions, but only 10% aerobically, raising the possibility that thiyl radical intermediates or glutathione disulfide products were undergoing further oxidation. Notably, the very high $O_2$ affinity of HMP (in the presence of NADH) may enable some higher oxidation of glutathione, despite best efforts to produce anaerobiosis. A reaction is proposed in which electrons are transferred to GSNO, yielding $NO^-$ and $GS^{31}$, which then form $N_2O$ and glutathione disulfide, respectively (equation 22).

$$2GSNO + NADH + H^+ \rightarrow 2GSSG + NAD^+ + N_2O + H_2O \qquad \text{Equ. 22}$$

Because nitroxyl anion ($NO^-$) is likely to be generated in this reaction, hydroxylamine might well be an alternative product in thiol-containing systems (Arnelle, D. R. & Stamler, J. S., *Arch. Biochem. Biophys.* 318:279–285 (1995)). Reductive metabolism of GSNO is probably catalyzed by the flavoreductase domain. This reaction, which like the oxygenase operated well at physiological concentrations (1–10 μM) of substrate, raised the possibility of an additional reductive mechanism for NO. Indeed, HMP catalyzed NO transformation into $N_2O$ anaerobically and the reaction was not inhibited by cyanide. However, the reduction of NO was ~250-fold slower that GSNO, raising the question of physiological relevance.

EXAMPLE 5

Demonstration of NADH-Dependent HMP-Induced Constriction of Blood Vessels Using Bioassay for Arterial Tone Methods Male New Zealand white rabbits (2–3 kg) were anaesthetized with intravenous sodium pentobartital (10 mg/kg), followed by exsanguination via the carotid artery. The descending thoracic aorta was dissected from the animal, taking care not to disrupt the intimal surface. The tissue was placed in ice-cold Krebs-bicarbonate buffer (pH 7.4) and used for bioassay experiments within 24 hours.

The aortic segment was carefully cleaned of all adventitial and adipose tissue and 3–4 mm rings were cut using a new scalpel blade. Rings were attached to isometric force transducers (FT01, Grass Instruments), connected to a multichannel polygraph recorder (Grass model 7a). The rings were then suspended in 25 ml jacketed organ chambers (Radnoti) containing Krebs-bicarbonate buffer aerated with 95% $O_2$ and 5% $CO_2$, pH 7.4, 37° C. Basal tension was gradually added to the vascular rings by a rack-and-pinion device to an optimum of 2 grams. Rings were then contracted with phenylephrine (PE; $10^{-7}$ M) and allowed to achieve a stable level of tone. At this point, acetylcholine (ACh; $10^{-7}$ to $10^{-6}$ M) was added to confirm the presence of a fully intact endothelium. When ACh-induced relaxation stabilized, the rings were flushed three times with fresh Krebs buffer and allowed to re-equilibrate back to baseline tone.

To determine the effects of HMP on vascular tone, rings were contracted with PE to a stable level of tone as described above. At this point, HMP (1–100 nM), in the absence or presence of 0.1 mM NADH, was added to the tissue chambers. Changes in tone can be represented as a percent change from the PE-induced tone. To determine the role of the vascular endothelium in the response to HMP, select aortic rings were subjected to endothelial disruption by rubbing the intimal surface with the shaft of a 22-gauge needle, followed by a 60 min. re-equilibration period. Removal of the endothelium can be confirmed by the loss of the relaxation response to ACh ($10^{-7}$ M) following contraction with PE. Responses to HMP±NADH were repeated as described above.

Results

FIG. 12A shows NADH-dependent HMP-induced constriction of blood vessels. Rabbit aortic ring segments were mounted on force transducers for measurement of isometric tone. Rings were preconstricted with phenylephrine (PE). HMP was then added at the indicated concentrations in the absence (left 4 traces) or presence (right 4 traces) of 0.1 mM NADH. For the tracings shown in FIG. 12B, EDRF/NO dependent relaxation was induced by addition of acetylcholine (ACh), 0.1 mM NADH and the indicated concentrations of HMP were then added. For the assay containing 100 nM HMP, a second dose of 0.1 mM NADH was made (arrow, FIG. 12A).

EXAMPLE 6

Measurement of Arteriolar Diameter and Blood Flow in Tumor in Rat Dorsal Flap Window Chamber Rat R3230Ac mammary adenocarcinomas were grown in a dorsal window flap chamber in Fischer 344 rats. Following anesthesia and cannulation of the femoral artery and vein, the window chamber was placed in a special plexiglass holder to stabilize the window. The rat was placed on a heated microscope stage for observation. An arteriole feeding the tumor was located and videotaped. Diameter was determined offline. A laser Doppler flowometry (LDF) probe was positioned underneath the tumor to determine tumor blood flow (TBF). These measurements were made for 30 minutes before infusion of HMP or vehicle and then for 60 minutes after the infusion. In this series of studies, two different doses of HMP were infused. Therefore, there were three experimental groups: vehicle control group, dose 1 group, and dose 2 group.

R3230Ac mammary adenocarcinomas were grown to 1 cm in diameter in the rat hindlimb. Under pentobarbital anesthesia, the femoral artery and vein was cannulated for monitoring of arterial blood pressure and for infusion of drug, respectively. A 2–3 mm piece of skin overlying the tumor was removed to expose the tumor surface. A 400 μm diameter laser Doppler flowometry (LDF) probe was inserted opposite the exposed surface to measure TBF. A second LDF probe was inserted into the quadriceps muscle adjacent to the tumor and a third was inserted into the deltoid muscle. A 6 to 15 μm tip diameter recessed tip oxygen microelectrode was inserted into the tumor through the exposed surface. A $PO_2$ value above zero was located and the electrode remained stationary throughout the rest of the experiment. Measurements of $PO_2$ and TBF were made under baseline conditions for 30 minutes. Then, HMP (25–100 mg) or vehicle was infused intravenously at a constant rate. The measurements were continued for another 60 minutes. Two doses of the agent or the vehicle were administered for a total of three groups. FIG. 14 shows that HMP infusion (t=0 min) reduces blood flow in a mammary adenocarcinoma model.

Methods To Be Used in Septic Shock Model (Examples 7 and 8)

New Zealand white rabbits (2–3 kg) are sedated with ketamine hydrochloride (50 mg/kg IM) and anaesthetized with sodium pentobarbital (30 mg/kg IV). Anesthesia is maintained by supplemental intravenous pentobarbital as needed. A tracheotomy is performed, and the trachea is intubated with a specifically designed endotracheal tube. Body temperature is maintained with a homeothermic blanket system (Harvard Apparatus Ltd.) and the femoral artery and vein are cannulated with polyethylene tubing (PE-90, Clay Adams). Arterial pressure is monitored with a pressure transducer (Cobe, Inc.) and recorded on a Gould physiograph (model RS-3800, Gould Electronics, Inc.). Rabbits are monitored for 20 minutes after surgery before beginning experimental protocols.

EXAMPLE 7

Effects of Lipopolysaccharide (LPS) on Arterial Pressure, Platelet cGMP and Total Plasma NO Content (Free NO+SNO) (Prophetic)

Animals are observed for 20 minutes to establish a stable hemodynamic state, and blood (4 ml) is obtained for total plasma NO and cGMP content. Animals are administered LPS (150 µg/kg IV for 1 minute); LPS administration is followed by blood sampling and arterial pressure recording at hourly intervals for a 6-hour period. Each blood sample is replaced with an equal volume of 0.9% saline to maintain volume status.

EXAMPLE 8

Effect of HMP±NADH on LPS Induced Septic Shock (Prophetic)

HMP can also be used in methods of therapy to reverse endotoxin-induced hypotension. A model system for testing the effects of HMP in septic shock can be used to demonstrate its effectiveness (Keaney, J. F. et al., *Circ. Res.* 74:1121–1125 (1994)).

After the establishment of a stable hemodynamic state, blood (4 ml) is obtained for determination of platelet cGMP and total plasma NO content. LPS (150 µg/kg) is administered as an intravenous bolus for 1 minute, and animals are observed for 3 hours or until mean arterial pressure falls to 55% of the baseline value. On achieving either end point, HMP will be serially administered intravenously at doses of 0.1, 1 and 10 µg/kg. Before the administration of HMP and 20 minutes after each dose, blood is drawn as described above. The effect of HMP±NADH alone will be established in 10 rabbits using the protocol above, except that saline placebo replaces LPS.

EXAMPLE 9

Tumor Growth Delay Study (Prophetic)

In these studies tumor bearing animals will be treated with HMP, a hypoxic cytotoxin, a combination of the two, or vehicle. Hypoxic cytotoxins show increased efficacy in hypoxic environments, so we hypothesize that decreasing perfusion and $PO_2$ in the tumor following administration of the cytotoxin will result in enhanced cell killing and significant tumor growth delay. In this study we will most likely use an alkylating agent (e.g., mitomycin C) as cytotoxin. Treatment will begin when the tumor reaches 7–8 mm diameter. The rats will first receive the cytotoxin or vehicle, followed by either HMP or the vehicle. The animals will be watched daily for signs of toxicity, and tumors will be measured three times a week. The endpoint that we use for tumor regrowth is 3 times the initial tumor volume. The time to reach this endpoint will be compared among the experimental groups. In this experiment, there will be five experimental groups with the rats receiving: 1) agent vehicle+ cytotoxin vehicle, 2) agent vehicle+cytotoxin, 3) agent+ cytotoxin vechicle, and 4) agent+cytotoxin.

The relevant teachings of all references cited herein are incorporated by reference.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of reducing the concentration of oxygen in an aqueous solution, comprising adding to the aqueous solution a reducing agent, a hemoprotein having deoxygenase activity and NO or a source of NO, and incubating the resulting solution under conditions suitable for deoxygenase activity.

2. A method of consuming NO in an aqueous solution, comprising adding an NO-consuming hemoprotein to the aqueous solution in the presence of $O_2$ and a reducing agent, and incubating the resulting solution under conditions suitable for NO-consuming activity by the hemoprotein.

3. The method of claim 2 wherein the NO-consuming hemoprotein is a flavohemoglobin.

* * * * *